(12) United States Patent
Hong et al.

(10) Patent No.: US 10,265,499 B2
(45) Date of Patent: Apr. 23, 2019

(54) COMPACT URINARY CATHETER

(71) Applicant: COMPACTCATH, INC., Palo Alto, CA (US)

(72) Inventors: Daniel Wei-Chen Hong, Cupertino, CA (US); Naama Stauber, San Francisco, CA (US)

(73) Assignee: COMPACTCATH, INC., Palo Alto, CA (US)

( * ) Notice: Subject to any disclaimer, the term of this patent is extended or adjusted under 35 U.S.C. 154(b) by 389 days.

(21) Appl. No.: 14/857,442

(22) Filed: Sep. 17, 2015

(65) Prior Publication Data

US 2016/0001037 A1    Jan. 7, 2016

Related U.S. Application Data

(63) Continuation-in-part of application No. 14/247,906, filed on Apr. 8, 2014, now abandoned, which is a
(Continued)

(51) Int. Cl.
*A61M 25/00* (2006.01)
*A61M 25/01* (2006.01)
(Continued)

(52) U.S. Cl.
CPC ....... *A61M 25/002* (2013.01); *A61M 25/0111* (2013.01); *A61M 27/00* (2013.01);
(Continued)

(58) Field of Classification Search
CPC .................................................. A61M 25/00
See application file for complete search history.

(56) References Cited

U.S. PATENT DOCUMENTS 2,711,734 A   6/1955  Moe
3,683,928 A   8/1972  Kuntz
(Continued)

FOREIGN PATENT DOCUMENTS

DE   20009506   10/2001
EP   0820781    1/1998
(Continued)

OTHER PUBLICATIONS

Partial International Search Report for PCT/US2012/040277, dated Jul. 20, 2012. (2 pages).

(Continued)

*Primary Examiner* — Benjamin J Klein
*Assistant Examiner* — Sara A Sass
(74) *Attorney, Agent, or Firm* — Merchant & Gould P.C.

(57) ABSTRACT

A urinary catheter system includes a catheter, a sheath, an enclosure and a plug. The catheter has distal and proximal ends. The sheath is slidable along the catheter between first and second positions. The enclosure encloses a majority of the catheter and includes a bottom member, a top member, an outer peripheral wall defining an outer hole to allow advancement of the distal end, and an inner peripheral wall defining an inner hole, where the catheter is extendable through the inner hole. Rotating the top or bottom member relative to the other member causes the catheter to wind within the enclosure. The plug can seal the proximal end to block liquid flow, and a user can disengage the plug to allow liquid flow.

6 Claims, 26 Drawing Sheets

Related U.S. Application Data continuation of application No. 13/916,215, filed on Jun. 12, 2013, now Pat. No. 8,708,999, which is a continuation of application No. 13/485,750, filed on May 31, 2012, now Pat. No. 8,556,884.

(60) Provisional application No. 61/491,492, filed on May 31, 2011, provisional application No. 62/052,490, filed on Sep. 19, 2014.

(51) Int. Cl.
| | | |
|---|---|---|
| *A61M 27/00* | (2006.01) | |
| *A61M 39/08* | (2006.01) | |
| *B65H 75/28* | (2006.01) | |
| *B65H 75/40* | (2006.01) | |
| *B65H 75/44* | (2006.01) | |

(52) U.S. Cl.
CPC ............ *B65H 75/28* (2013.01); *B65H 75/40* (2013.01); *B65H 75/4481* (2013.01); *A61M 25/0097* (2013.01); *A61M 2025/0018* (2013.01); *A61M 2039/087* (2013.01); *B65H 2701/33* (2013.01)

(56) References Cited

U.S. PATENT DOCUMENTS

| | | | |
|---|---|---|---|
| 3,806,992 A | 4/1974 | Reimer | |
| 4,160,451 A | 7/1979 | Chittenden | |
| 4,244,536 A | 1/1981 | Harrill | |
| 4,311,050 A | 1/1982 | Bessman | |
| 4,384,688 A | 5/1983 | Smith | |
| 4,467,979 A | 8/1984 | Koehler | |
| 4,656,320 A | 4/1987 | Maddock | |
| 4,811,847 A | 3/1989 | Reif et al. | |
| 4,835,003 A | 5/1989 | Becker et al. | |
| 4,850,974 A * | 7/1989 | Bickelhaupt | A61M 25/0113 604/171 |
| 4,903,826 A | 2/1990 | Pearce | |
| 4,921,096 A | 5/1990 | McFarlane | |
| 5,103,977 A | 4/1992 | Douglas | |
| 5,125,416 A | 6/1992 | Phillips | |
| 5,344,011 A | 9/1994 | DiBernardo et al. | |
| 5,372,254 A | 12/1994 | Gross | |
| 5,392,918 A | 2/1995 | Harrison | |
| 5,421,457 A | 6/1995 | Listenberger | |
| 5,730,150 A | 3/1998 | Peppel et al. | |
| 5,738,213 A | 4/1998 | Whiting et al. | |
| 5,769,222 A | 6/1998 | Banerian | |
| 5,915,640 A | 6/1999 | Wagter et al. | |
| 5,915,641 A | 6/1999 | Barberg | |
| 6,056,226 A | 5/2000 | Green | |
| 6,086,008 A * | 7/2000 | Gray | A61M 25/0113 242/388.6 |
| 6,375,006 B1 | 4/2002 | Samuels | |
| 6,719,135 B2 | 4/2004 | Armijo | |
| 6,902,057 B2 | 6/2005 | Duffy | |
| 7,191,900 B2 | 3/2007 | Opie et al. | |
| 7,234,597 B2 | 6/2007 | Rowe et al. | |
| 7,549,270 B2 | 6/2009 | Rowe et al. | |
| 7,640,714 B2 | 1/2010 | Waller et al. | |
| 7,682,353 B2 | 3/2010 | Tanghoj et al. | |
| 7,766,162 B2 * | 8/2010 | Maki | A61M 25/002 206/364 |
| 7,789,873 B2 | 9/2010 | Kubalak et al. | |
| 7,867,220 B2 | 1/2011 | Tanghoj | |
| 7,922,712 B2 | 4/2011 | Tanghoj et al. | |
| 8,556,884 B2 * | 10/2013 | Hong | A61M 25/0017 242/159 |
| 8,651,412 B2 * | 2/2014 | Hernik | B65H 75/4481 242/588.3 |
| 8,708,999 B2 | 4/2014 | Hong | |
| 8,974,438 B2 | 5/2015 | Hong | |
| 9,023,013 B2 * | 5/2015 | Schertiger | A61M 25/0111 206/364 |
| 2002/0145073 A1 | 10/2002 | Swanson et al. | |
| 2003/0015617 A1 | 1/2003 | Chuang | |
| 2004/0055919 A1 | 3/2004 | Rowe et al. | |
| 2005/0109648 A1 | 5/2005 | Kerzman et al. | |
| 2006/0016480 A1 | 1/2006 | Cheng | |
| 2006/0048819 A1 | 3/2006 | Dean | |
| 2006/0058777 A1 | 3/2006 | Nielsen | |
| 2006/0142737 A1 | 6/2006 | Tanghoj | |
| 2006/0186256 A1 | 8/2006 | Mogensen et al. | |
| 2006/0260968 A1 | 11/2006 | Mayda, II et al. | |
| 2006/0271019 A1 | 11/2006 | Stoller et al. | |
| 2007/0088330 A1 | 4/2007 | House | |
| 2008/0017745 A1 | 1/2008 | Laga | |
| 2009/0054876 A1 | 2/2009 | Borodulin et al. | |
| 2009/0071851 A1 | 3/2009 | Maki et al. | |
| 2009/0137985 A1 | 5/2009 | Tanghoj et al. | |
| 2009/0149837 A1 * | 6/2009 | Tanghoj | A61F 5/44 604/544 |
| 2009/0200187 A1 | 8/2009 | Nestenborg et al. | |
| 2009/0204106 A1 | 8/2009 | Golden | |
| 2009/0208368 A1 | 8/2009 | Waldrep et al. | |
| 2009/0277988 A1 | 11/2009 | Hernik | |
| 2010/0087801 A1 | 4/2010 | Torstensen et al. | |
| 2010/0130923 A1 | 5/2010 | Cleary et al. | |
| 2014/0221983 A1 | 8/2014 | Hong | |

FOREIGN PATENT DOCUMENTS

| | | |
|---|---|---|
| EP | 1023882 | 8/2000 |
| WO | WO98-56687 | 12/1998 |
| WO | WO01-78824 | 10/2001 |
| WO | WO2004-022433 | 3/2004 |
| WO | WO2004-054653 | 7/2004 |
| WO | WO2007-081264 | 7/2007 |
| WO | WO2008-089770 | 7/2008 |
| WO | WO2012-166967 | 12/2012 |

OTHER PUBLICATIONS

International Search Report and Written Opinon for PCT/US2012/040277, dated Sep. 10, 2012, 20 pages.

* cited by examiner

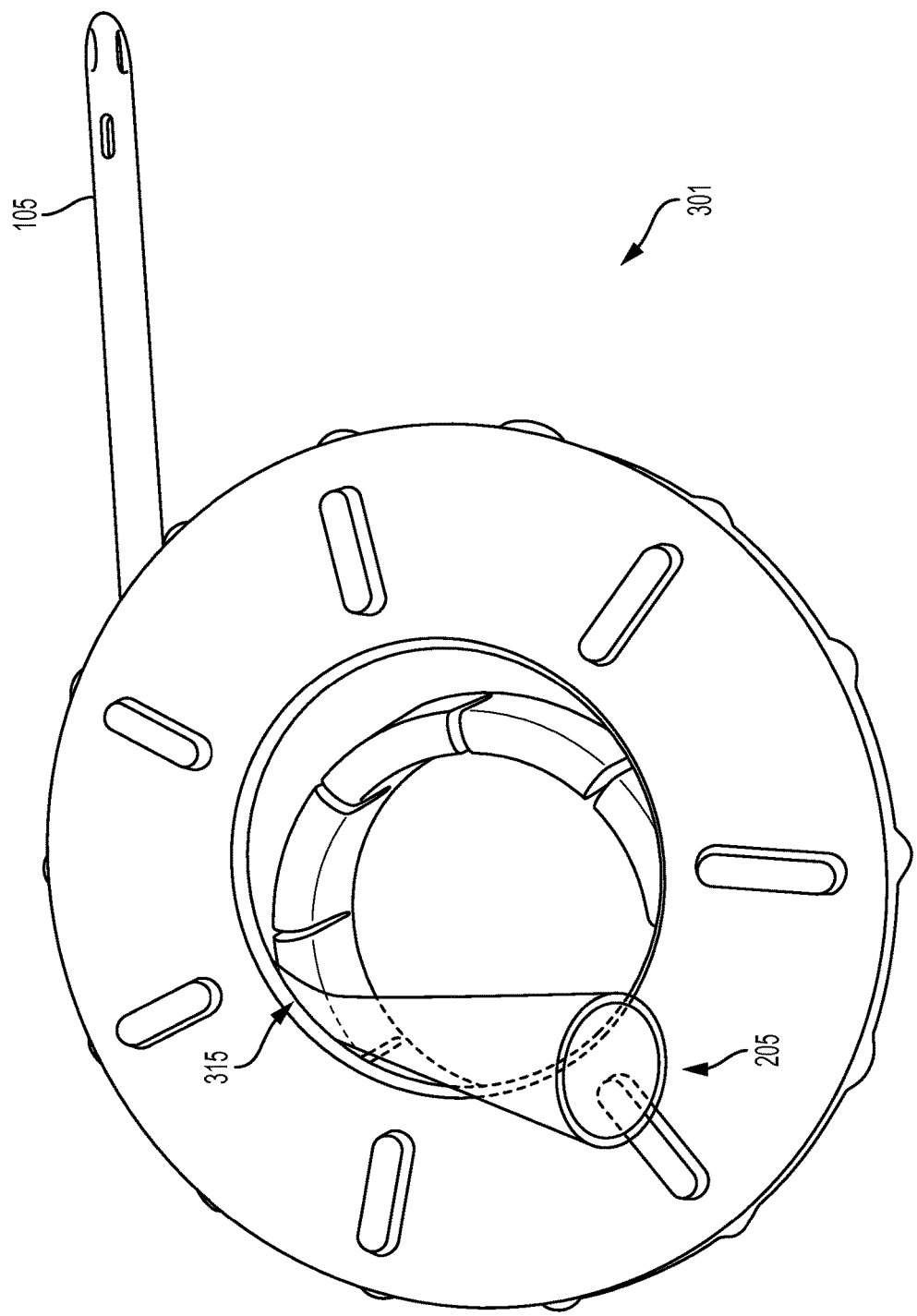

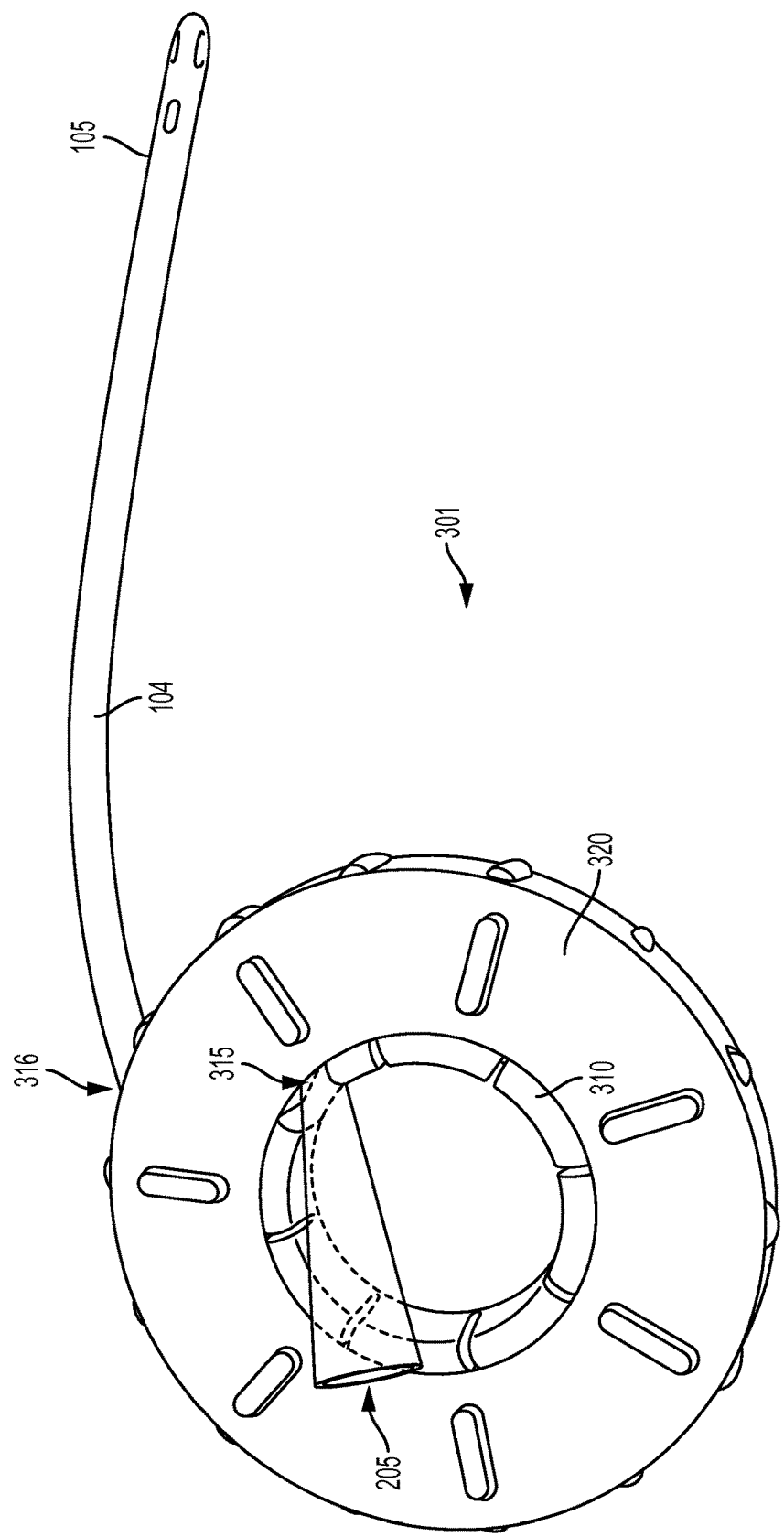

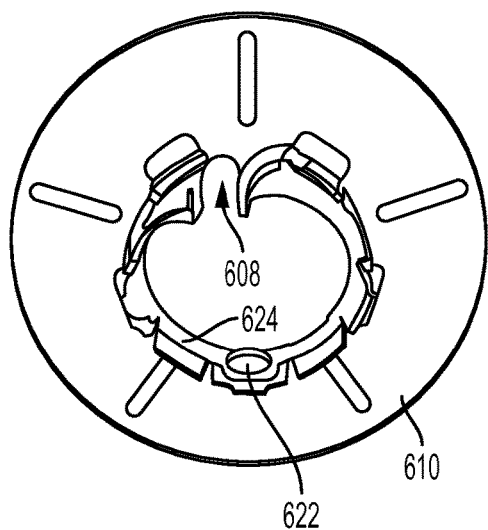
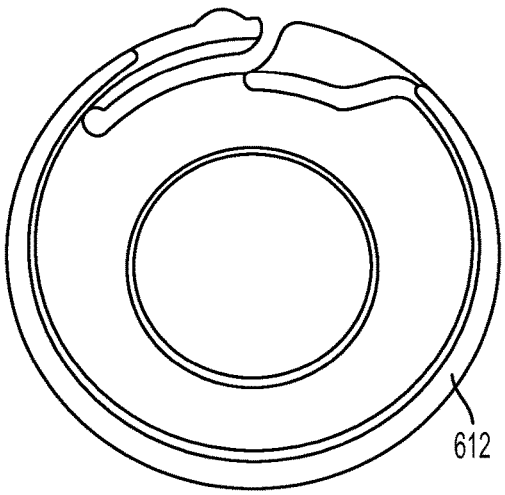
FIG. 6A  FIG. 6B
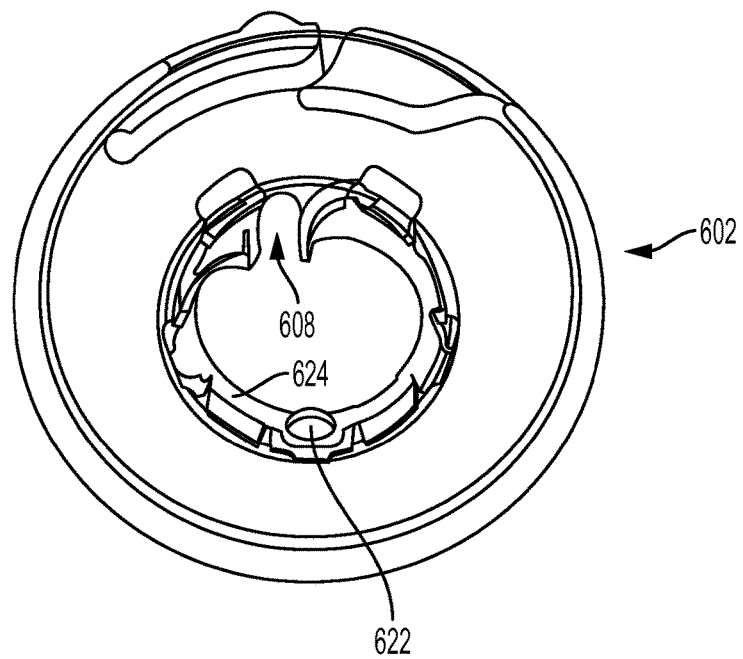
FIG. 6C

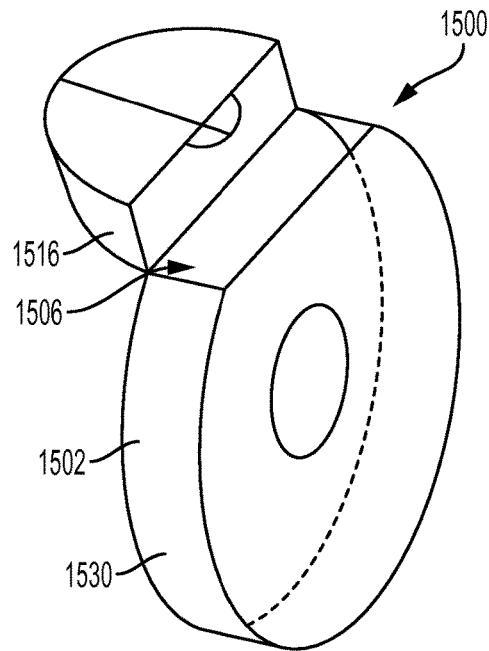
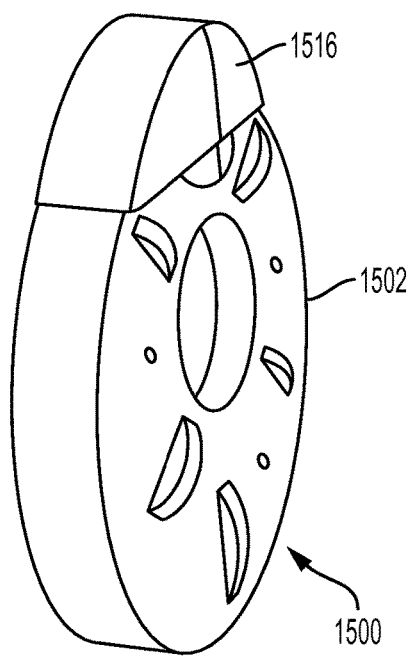
FIG. 15A  FIG. 15B
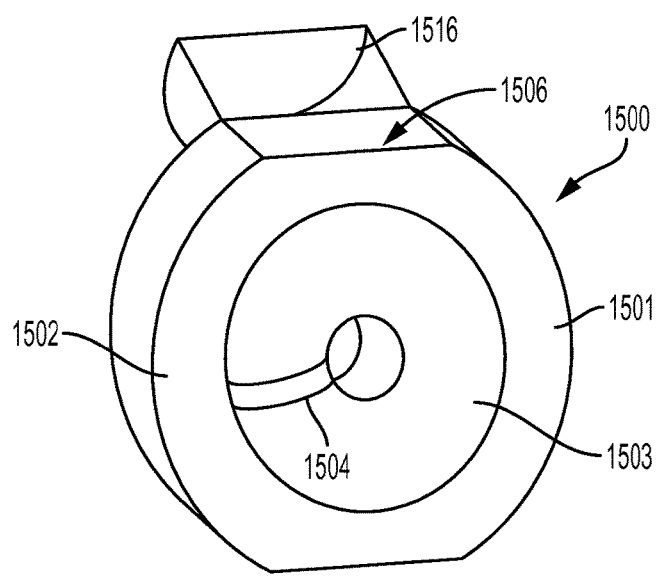
FIG. 15C

COMPACT URINARY CATHETER

CROSS-REFERENCE TO RELATED APPLICATIONS

This application is a continuation-in-part of pending U.S. patent application Ser. No. 14/247,906, filed Apr. 8, 2014, entitled "Compact Catheter Assembly," which is a continuation application of U.S. patent application Ser. No. 13/916,215 filed Jun. 12, 2013, entitled "Compact Catheter Assembly," now U.S. Pat. No. 8,708,999, which is a continuation application of U.S. patent application Ser. No. 13/485,750, filed May 31, 2012, entitled "Compact Catheter Assembly," now U.S. Pat. No. 8,556,884, and which claims priority to U.S. Provisional Patent Application Ser. No. 61/491,492, filed May 31, 2011. This application claims priority to U.S. Provisional Patent Application Ser. No. 62/052,490 filed Sep. 19, 2014, entitled, "Compact Urinary Catheter." The above-referenced applications are hereby incorporated by reference as if fully set forth herein.

BACKGROUND

Field of the Disclosure

This application generally relates to urinary catheters, assemblies including urinary catheters, and medical uses thereof.

Background of the Disclosure

Some patients require urinary catheters to effectively and hygienically void their bladder, such as those patients who suffer from urinary incontinence or other medical disorders.

Urinary catheters are inserted into the bladder through the urethra in order to open the urinary sphincter and drain urine into an appropriate receptacle. A typical urinary catheter patient might void their bladder every two to four hours. In developed countries, urinary catheters are disposable (that is, they are not reused), with the effect of requiring the use of multiple catheters per day.

It sometimes occurs that urinary catheters for patient use are insufficiently compact, or otherwise involve relatively bulky equipment. For example, in current use, many catheters are packaged in an elongated form, with the effect that they are cumbersome for both storage and transport. This can have the effect that the urinary catheter, or its presence on the patient, is readily apparent, or is not easily conveyed by the patient or in the patient's clothing when in use, or is not easily concealed or otherwise attached to the patient's clothing when in use.

Similarly, it sometimes occurs that using a urinary catheter has the substantial possibility of social embarrassment for the patient due to the possibility of the catheter, or any associated medical equipment, or the fact of the patient's need for the urinary catheter, becoming observed in a social setting. This can also occur due to the urinary catheter, or its presence on the patient, becoming apparent, or not being well concealed by the patient's clothing. More recently, smaller and more discreet catheters have been developed, such as the "SpeediCath™ Compact" catheter by Coloplast, Inc.

It sometimes occurs that it is difficult to handle lubricated catheters, as they are often designed to be slippery, so as to facilitate easy insertion into the urethra. For example, in current use, many catheters are either pre-lubricated with a water activated coating, or are designed to be lubricated with a gel after opening, in either case in order to make it easier for the urinary catheter to be inserted into the urethra. Moreover, these lubricating mechanisms can be inconvenient, as users must either deal with packaging fluid, or carry around a lubricant along with the urinary catheter.

It also sometimes occurs that using a urinary catheter can be unhygienic due to the possibility of touching the catheter with an unsanitary object, such as either the patient's hand, or a portion of the patient's body other than for insertion into the urethra. This can have more than one untoward effect. A first effect can be that use of an unhygienic urinary catheter might lead to a urinary tract infection, or other untoward medical condition. For example, when handling the catheter directly, users must generally ensure that their hands and the opening of the urethra are clean, in order to avoid contaminating the catheter and risking a urinary tract infection. A second effect can be that the urinary catheter must be disposed of after use, and replaced with another such catheter, with the concomitant difficulty of needing additional urinary catheters, as well as some form of storage for used catheters.

Also, many of the currently available catheters require the user to detach and use a part of the catheter packaging to handle the catheter. However, the detachment process itself can be quite challenging. The fact that urinary catheters are conspicuous and difficult to use may lead to serious problems, since a self-conscious user may not be inclined to use them in certain social settings, leading to bladder and/or kidney problems when urine is not voided in the right frequency.

BRIEF SUMMARY OF THE DISCLOSURE

This application provides techniques, including devices, assemblies, and methods, which include compact packaging systems for urinary catheters, and use thereof.

In some embodiments, a urinary catheter and enclosure system is disclosed. The system includes a urinary catheter, a sheath, an enclosure, and a plug. The urinary catheter has a distal end configured for insertion into a urethra and a proximal end. The sheath surrounds a portion of the catheter proximate the distal end, the sheath being slidable by a user along the catheter in the longitudinal direction between a first position and a second position. The enclosure is for enclosing a majority of the urinary catheter. The enclosure includes a bottom member comprising a bottom surface, a top member comprising a top surface and engaged with the bottom member so to rotate relative to the bottom member about an axis of rotation, an outer peripheral wall, and an inner peripheral wall. The outer peripheral wall extends from the bottom surface to the top surface along an outer peripheral portion of the enclosure, the outer peripheral wall defining an outer hole configured to allow advancement of the catheter distal end therethrough. The inner peripheral wall extends from the bottom surface to the top surface along an inner peripheral portion of the enclosure, the inner peripheral wall defining an inner hole. The catheter extends through the inner hole so that the proximal end is located outside of the enclosure. Rotating one of the top member or the bottom member relative to the other member causes the catheter to wind into a spiral within the enclosure. The plug is configured to seal the proximal end of the catheter to block liquid flow therethrough, and a user can disengage the plug from the catheter to allow fluid flow through the proximal end.

In some embodiments, disclosed is a method for using a compact urinary catheter assembly to void a bladder of a human or animal subject. The method includes grasping a sheath surrounding a portion of a catheter at a first position at or near a distal end of the catheter, wherein a majority of the catheter is housed in an enclosure comprising a top member and a bottom member, and wherein the distal end of the catheter is located outside an outer hole in the enclosure. The method includes advancing the catheter out of the enclosure by pulling on the catheter via the grasped sheath, and sliding the sheath proximally along the catheter to a second position. The method includes advancing the distal end of the catheter into a urethra of the subject, and disengaging a plug from a proximal end of the catheter to unblock liquid flow therethrough, wherein the proximal end of the catheter is located outside an inner hole in the enclosure. The method includes voiding the bladder through the catheter while a length of the catheter remains within the enclosure, so that urine passes from the bladder of the subject into the distal end of the catheter and out of the proximal end of the catheter.

BRIEF DESCRIPTION OF THE FIGURES

While the specification concludes with claims particularly pointing out and distinctly claiming the subject matter that is regarded as forming the present disclosure, it is believed that the disclosure will be better understood from the following description taken in conjunction with the accompanying Figures, in which:

FIB. 3C shows a conceptual drawing of un assembled top and bottom elements of a catheter assembly.

FIG. 3D shows a conceptual drawing of an assembled catheter assembly.

Figure 3A:
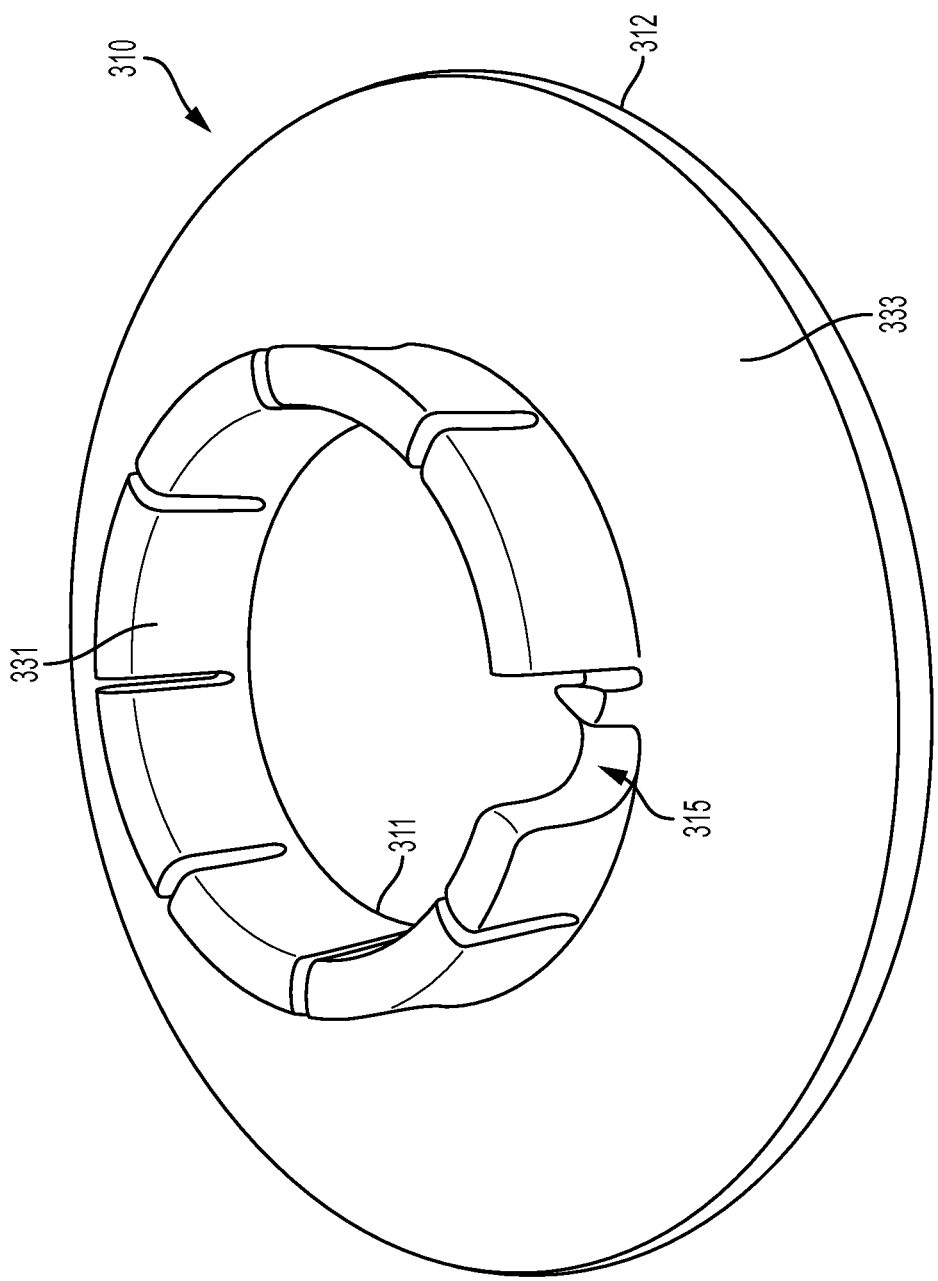
FIG. 3A shows a conceptual drawing of a bottom element of a catheter assembly.
Figure 3B:
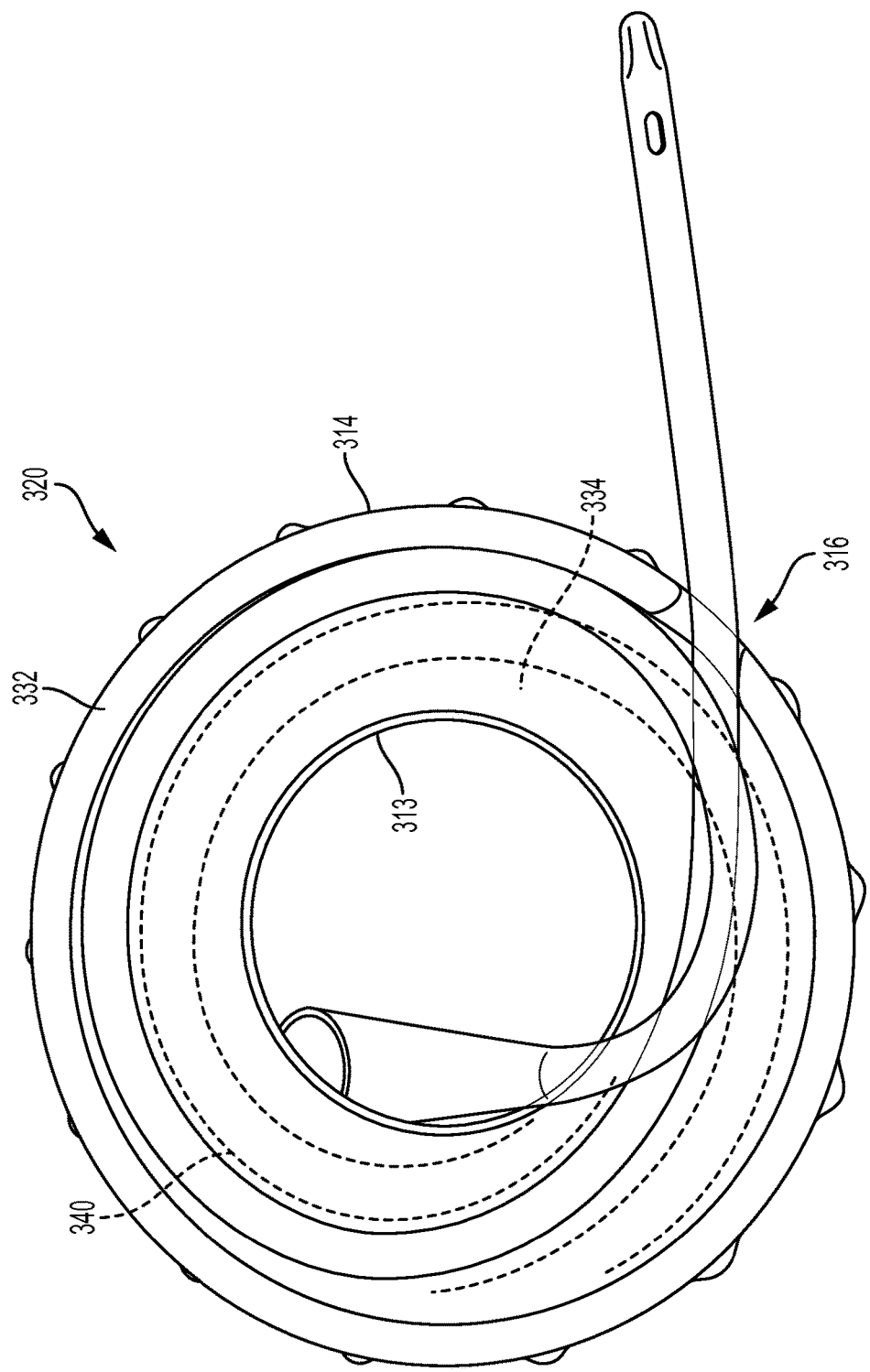
FIG. 3B shows a conceptual drawing of a top element of a catheter assembly.
Figure 3E:
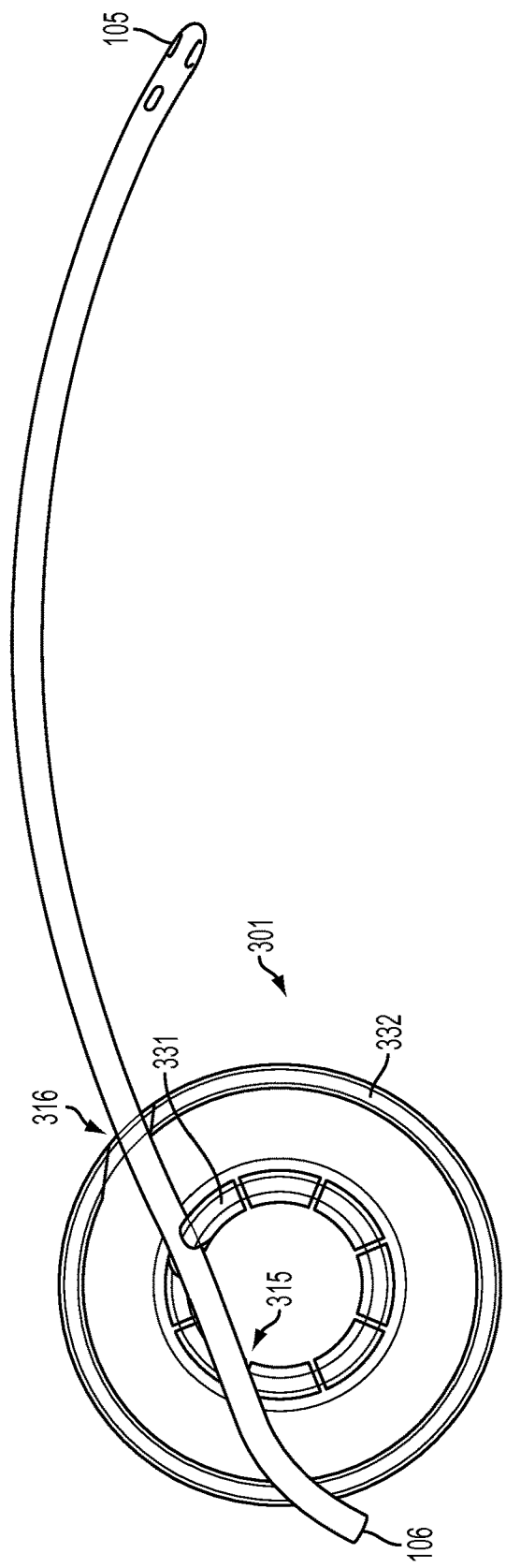

FIG. 3E s shows a conceptual drawing of a bottom element of a catheter assembly with a catheter attached thereto.

Figure 4:
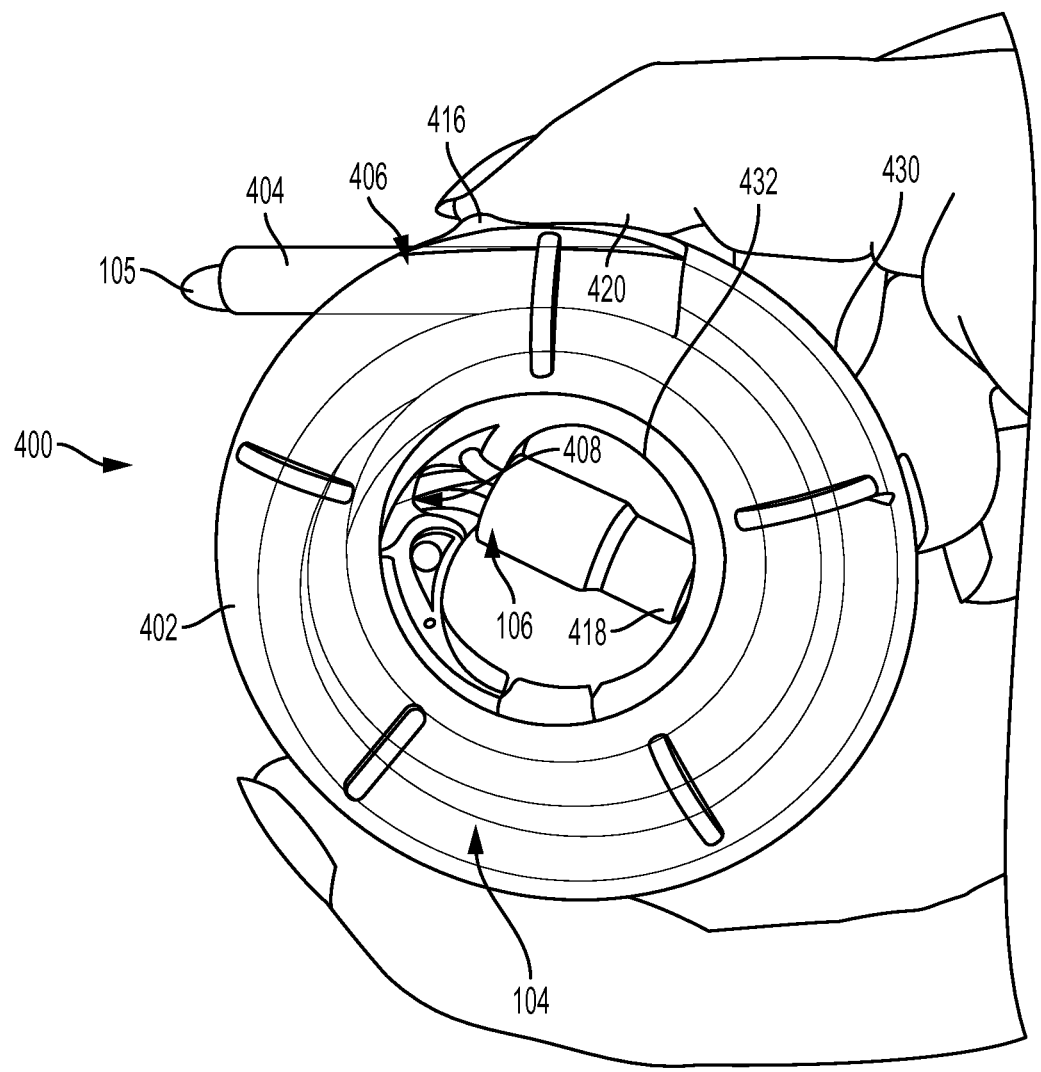

FIG. 4 shows a conceptual drawing of a urinary catheter and enclosure system.

Figure 5A:
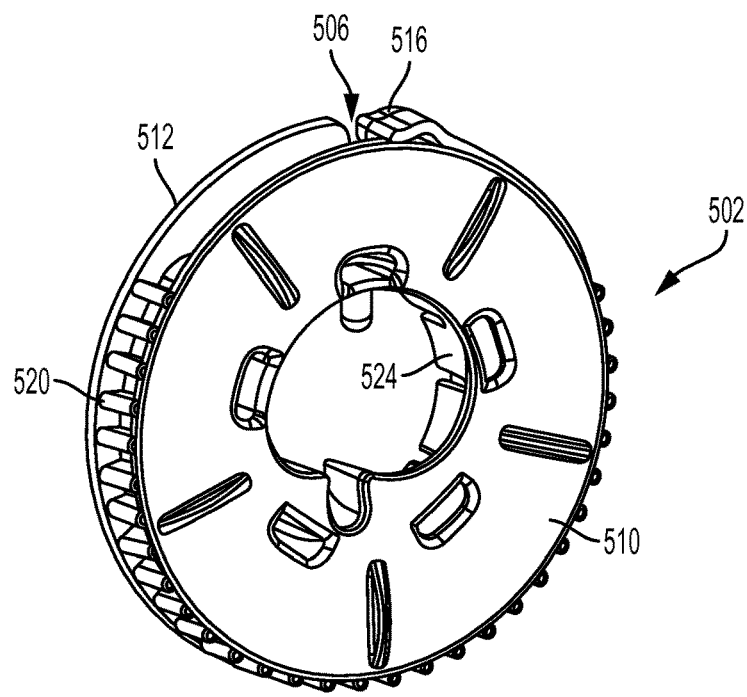

FIG. 5A shows a conceptual drawing of an enclosure.

Figure 5B:
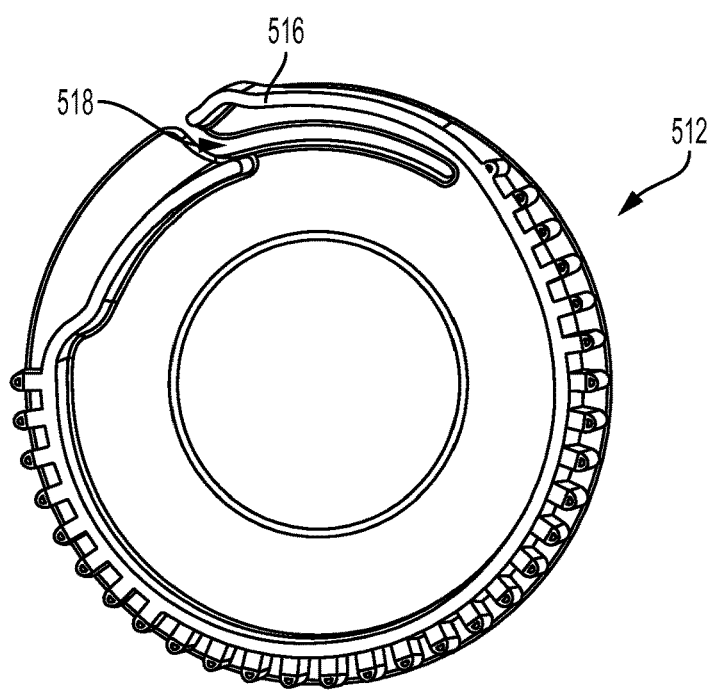

FIG. 5B shows a conceptual drawing of a top member of an enclosure.

FIG. 6A shows a conceptual drawing of a bottom member of an enclosure.

FIG. 6B shows a conceptual drawing of a top member of an enclosure.

FIG. 6C shows a conceptual drawing of assembled bottom and top members of an enclosure.

Figure 7A:
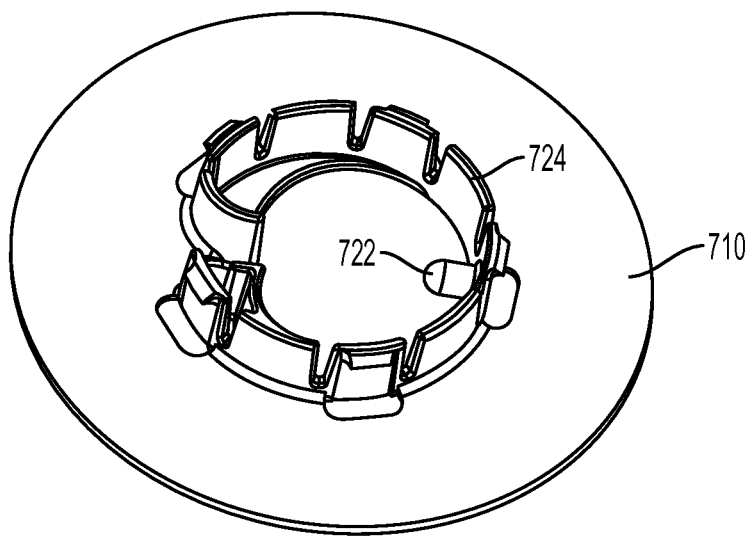

FIG. 7A shows a conceptual drawing of a top perspective view of a bottom member of an enclosure.

Figure 7B:
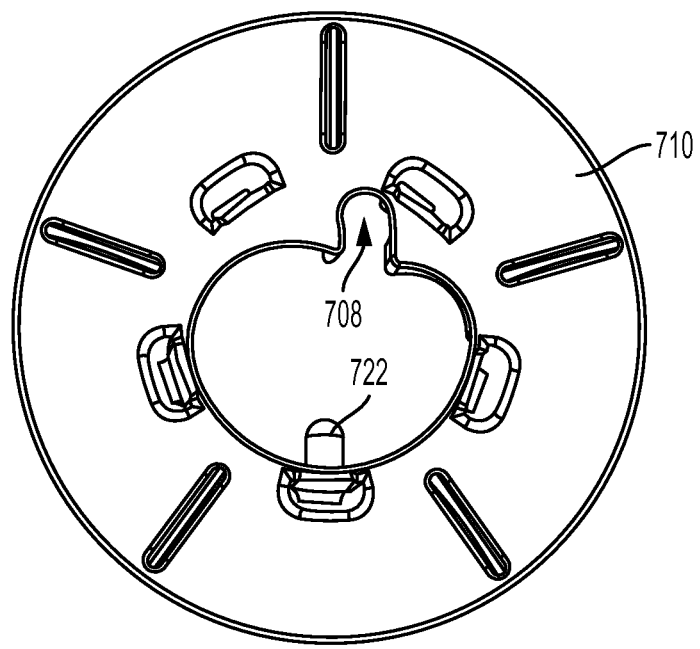

FIG. 7B shows a conceptual drawing of a bottom view of a bottom member of an enclosure.

Figure 8:
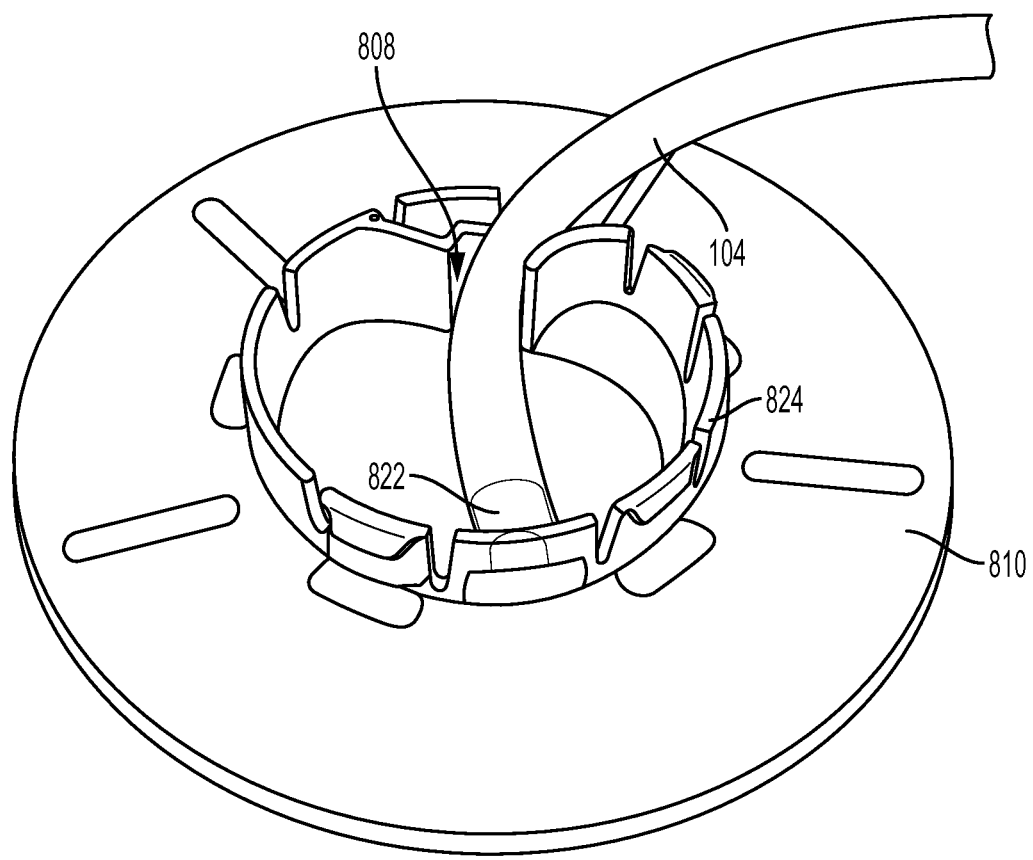

FIG. 8 shows a conceptual drawing a bottom member of an enclosure and a urinary catheter attached thereto.

Figure 9A:
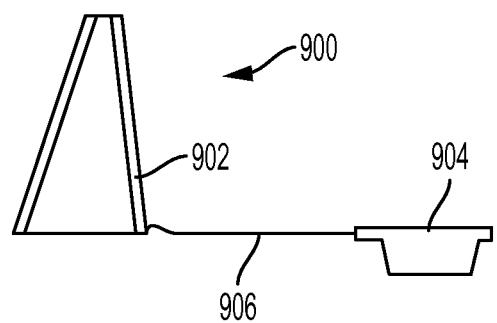
Figure 9B:
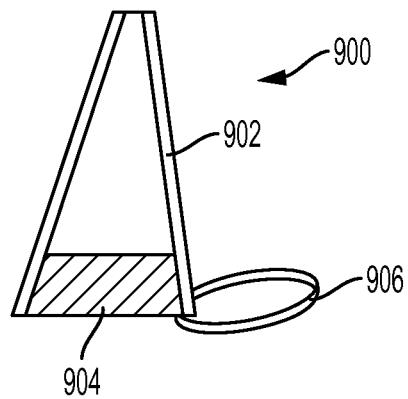
Figure 9C:
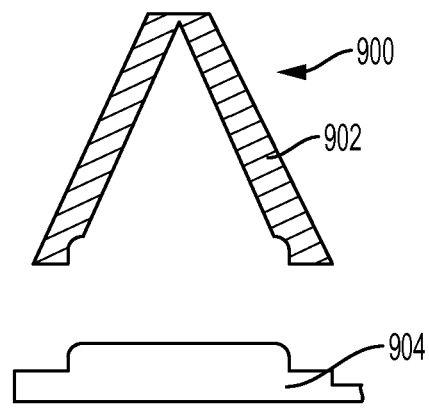

FIGS. 9A-9C show conceptual drawing of a plug and funnel arrangement.

Figure 10A:
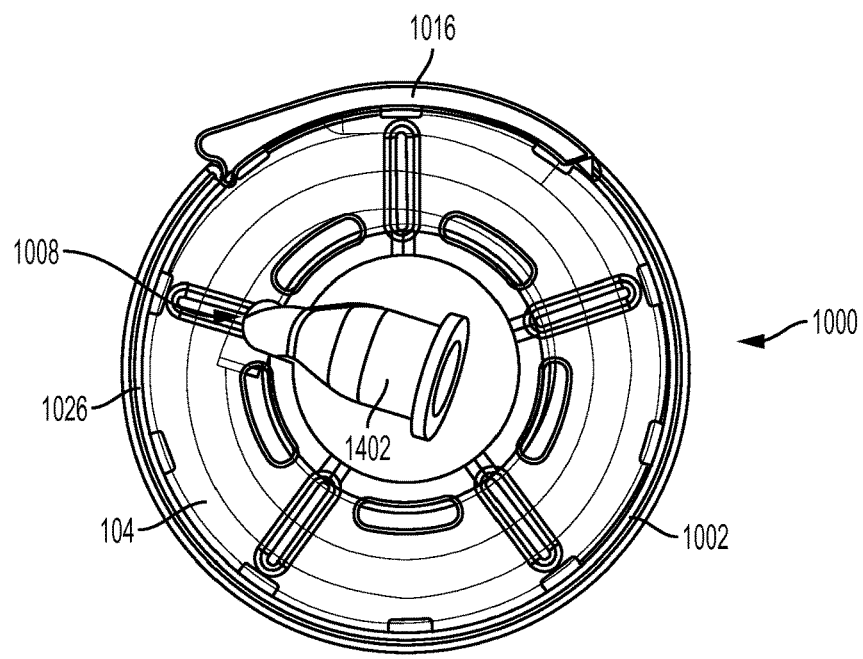

FIG. 10A shows a conceptual drawing of a urinary catheter and enclosure system in a closed configuration.

Figure 10B:
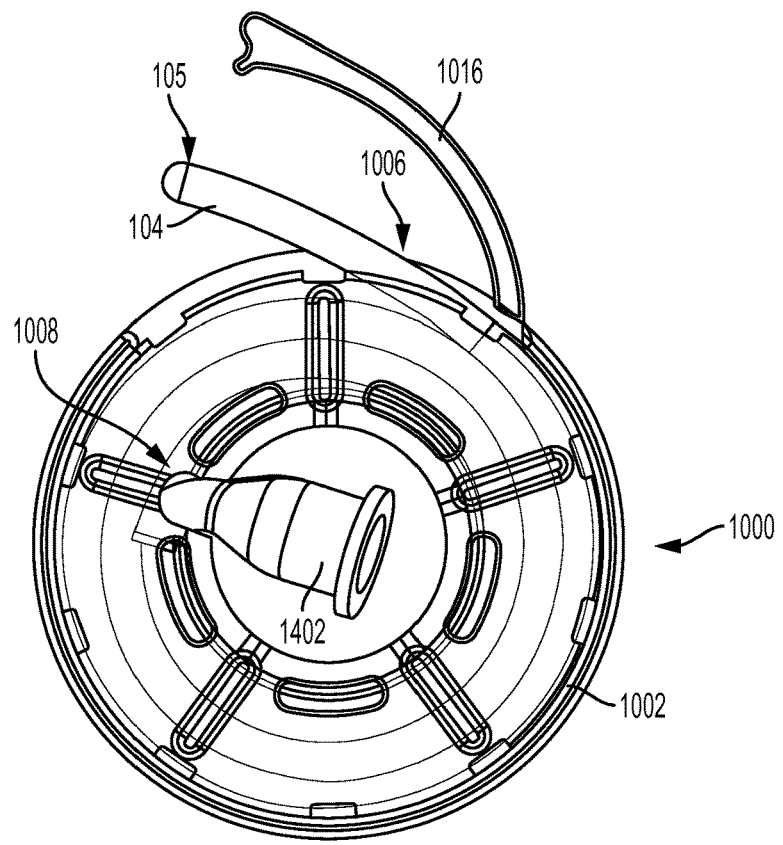

FIG. 10B shows a conceptual drawing of a urinary catheter and enclosure system in an open configuration.

Figure 11:
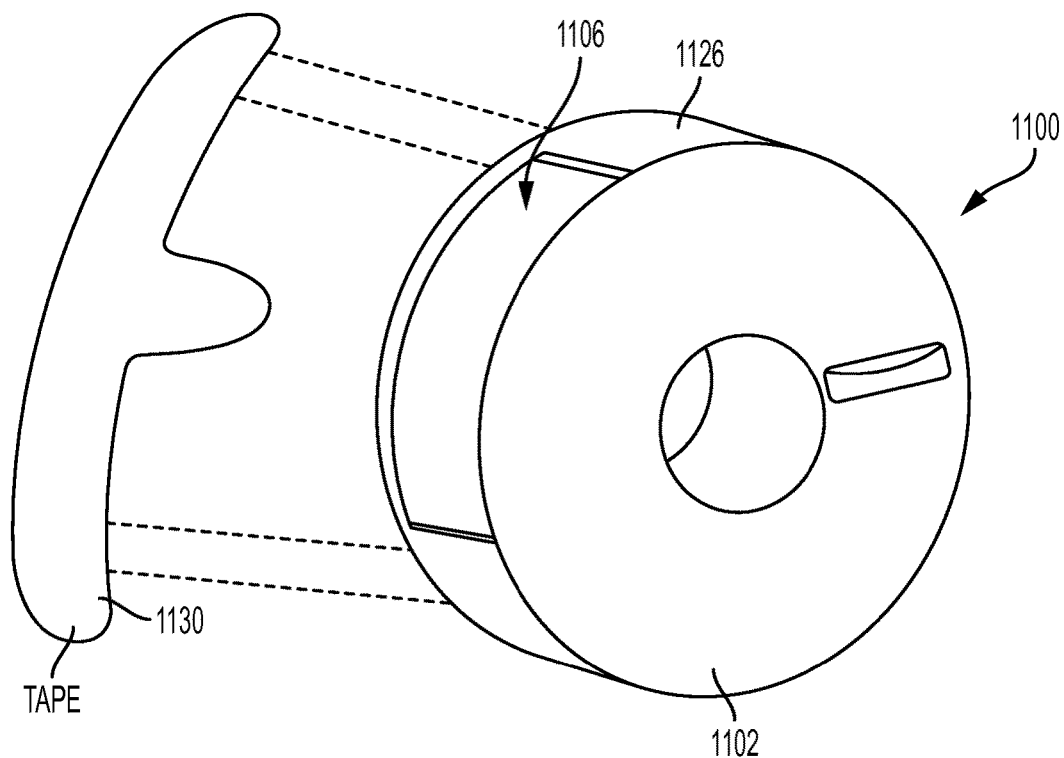
Figure 12A:
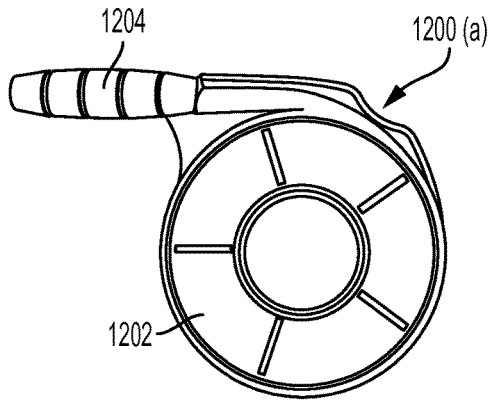
Figure 12B:
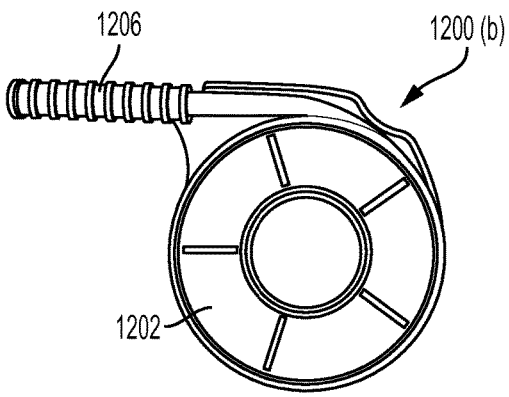
Figure 12C:
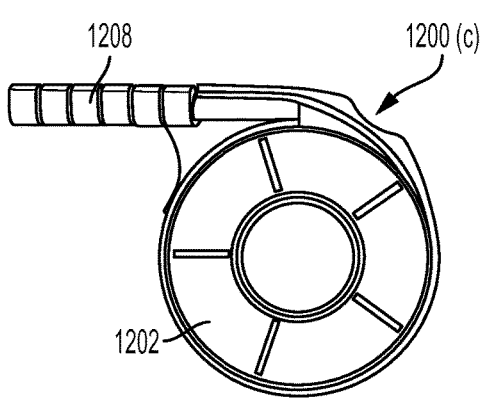
Figure 12D:
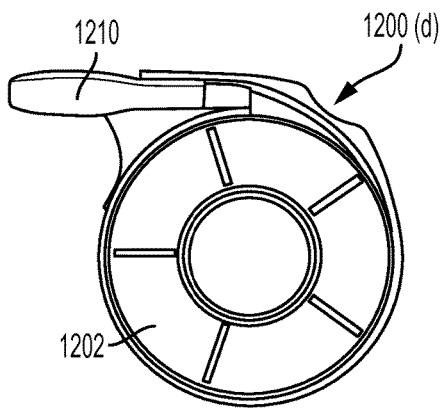
Figure 12E:
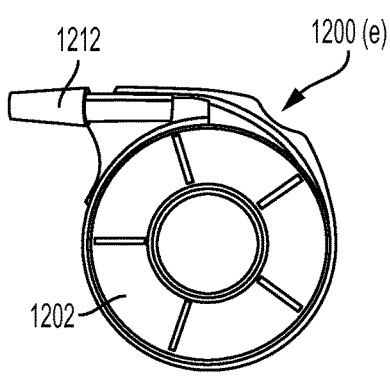
Figure 12F:
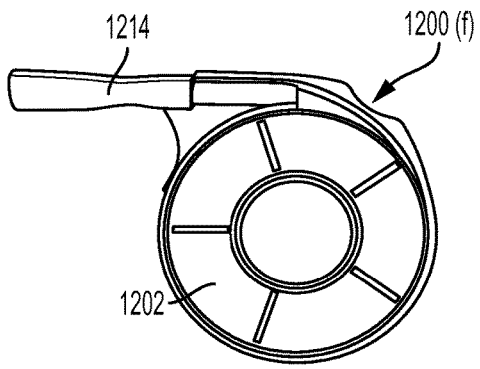

FIG. 11 shows a conceptual drawing of an enclosure.

FIGS. 12A-12F show conceptual drawings of hygiene sheaths, according to certain embodiments.

Figure 13:
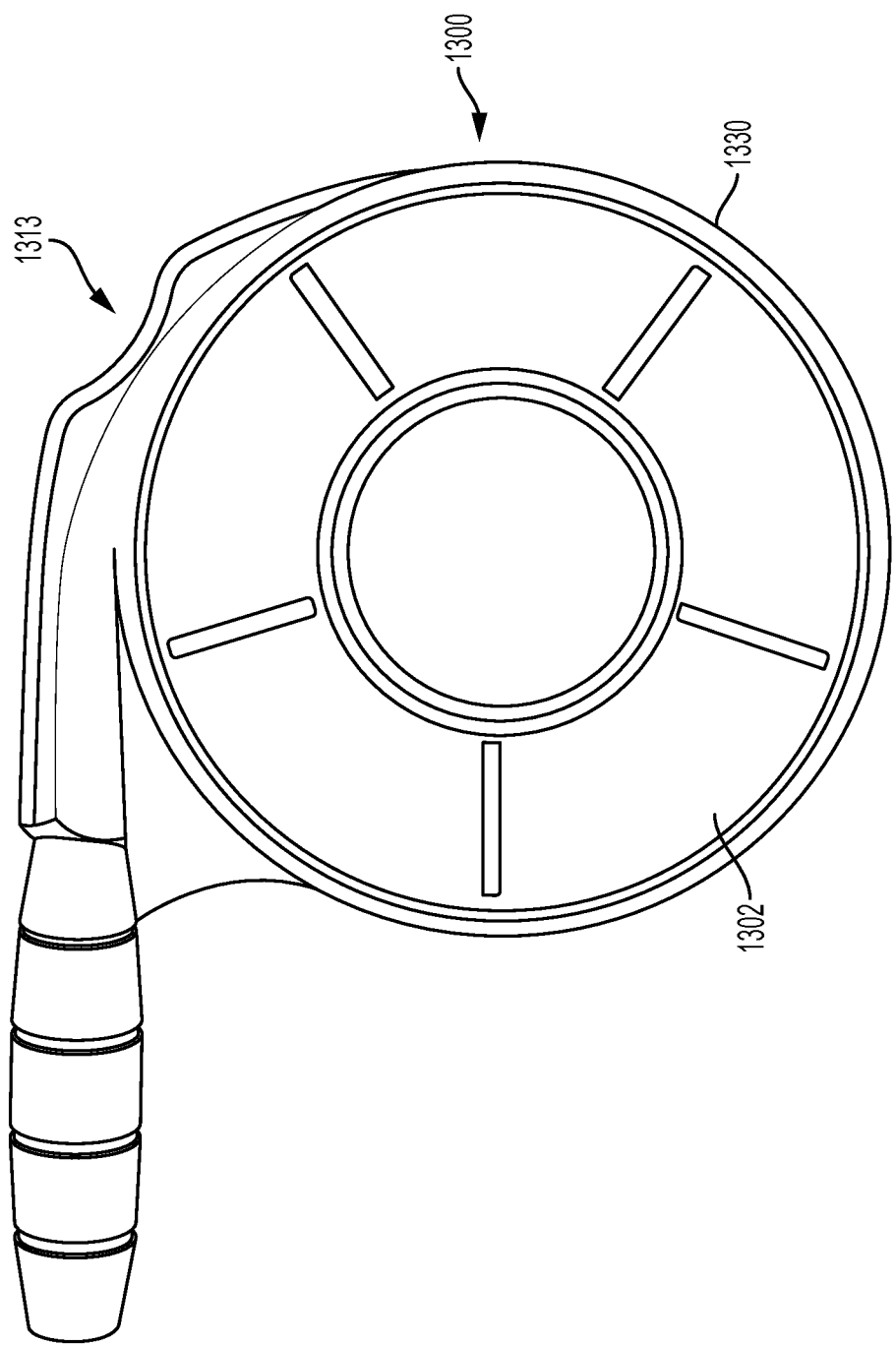

FIG. 13 shows a conceptual drawing of a urinary catheter and enclosure system.

Figure 14:
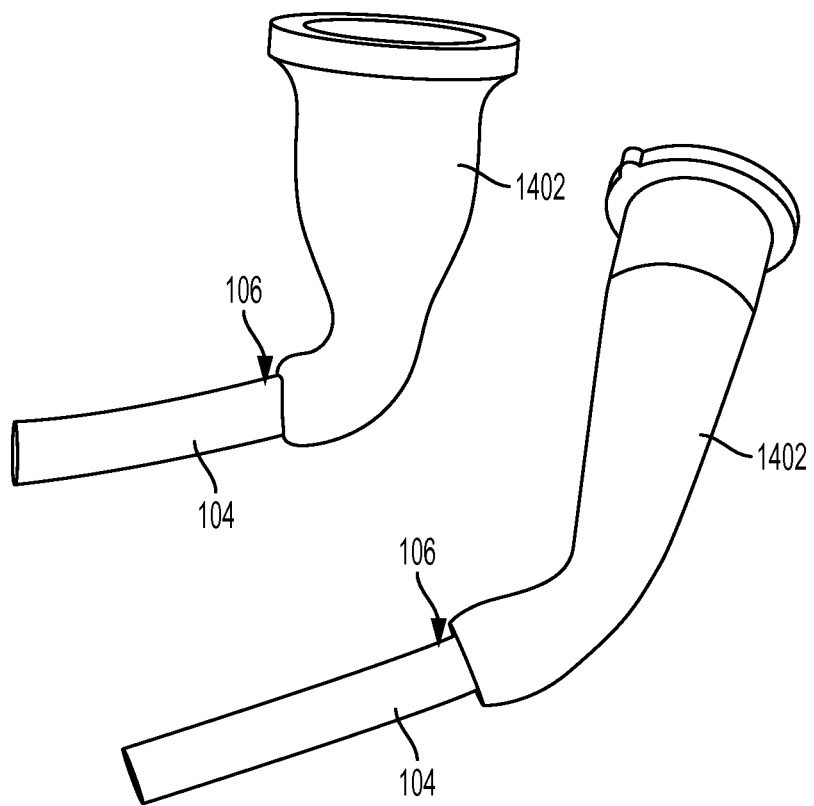

FIG. 14 shows a conceptual drawing of funnels.

FIGS. 15A-15C show conceptual drawings of an enclosure.

Figure 16A:
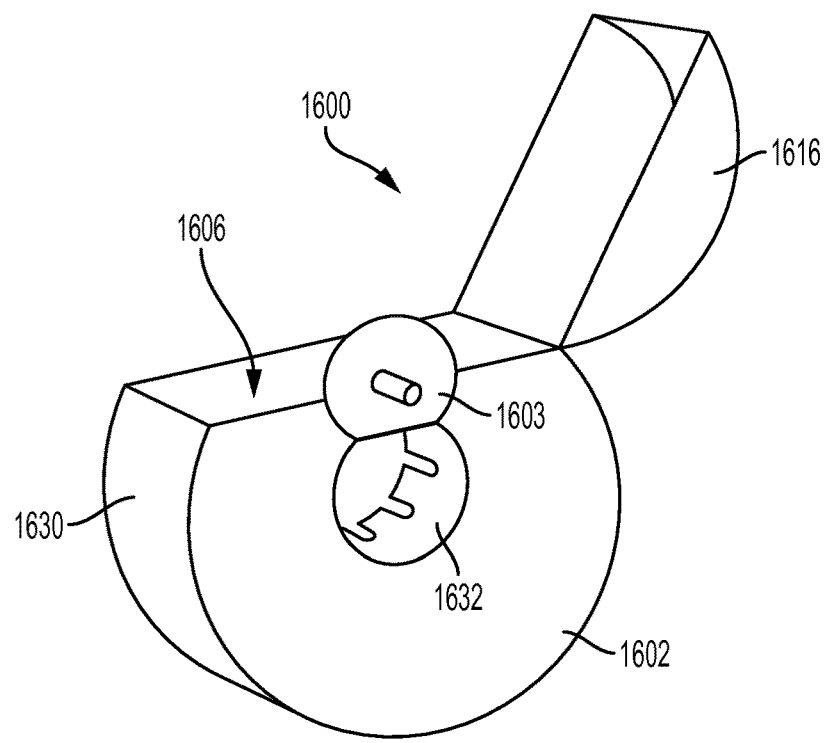

FIG. 16A shows a conceptual drawing of an enclosure.

Figures 16B, 16C:
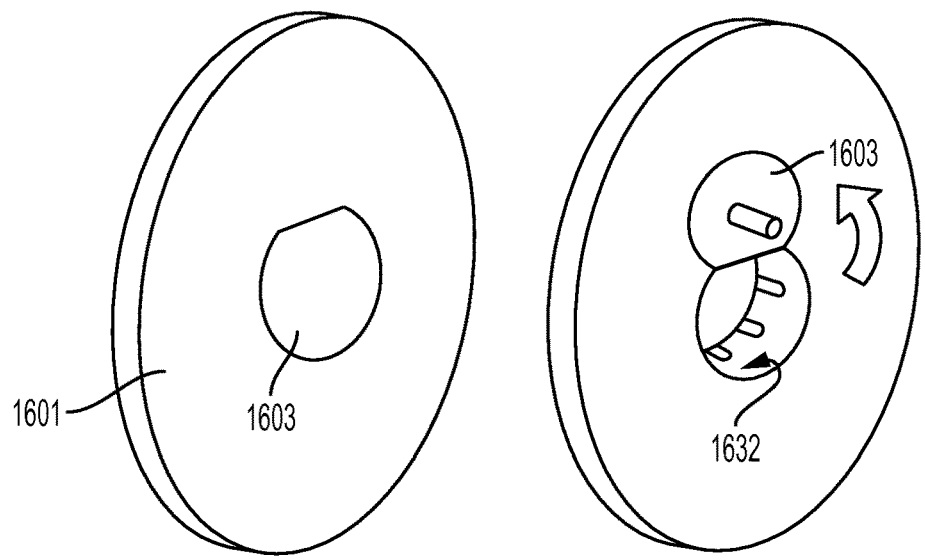

FIG. 16B shows a conceptual drawing of a bottom member of an enclosure.

FIG. 16C shows a conceptual drawing of a bottom member of an enclosure.

Figure 17:
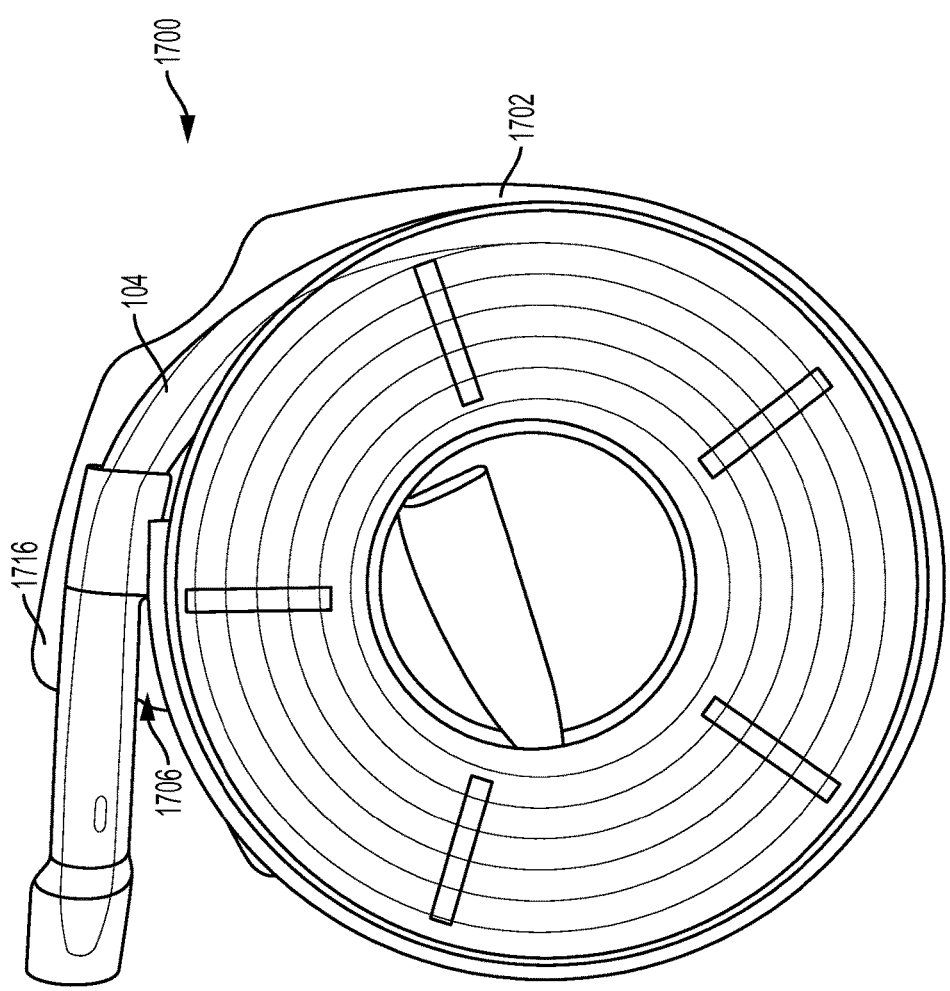

FIG. 17 shows a conceptual drawing of a urinary catheter and enclosure system.

Figure 18:
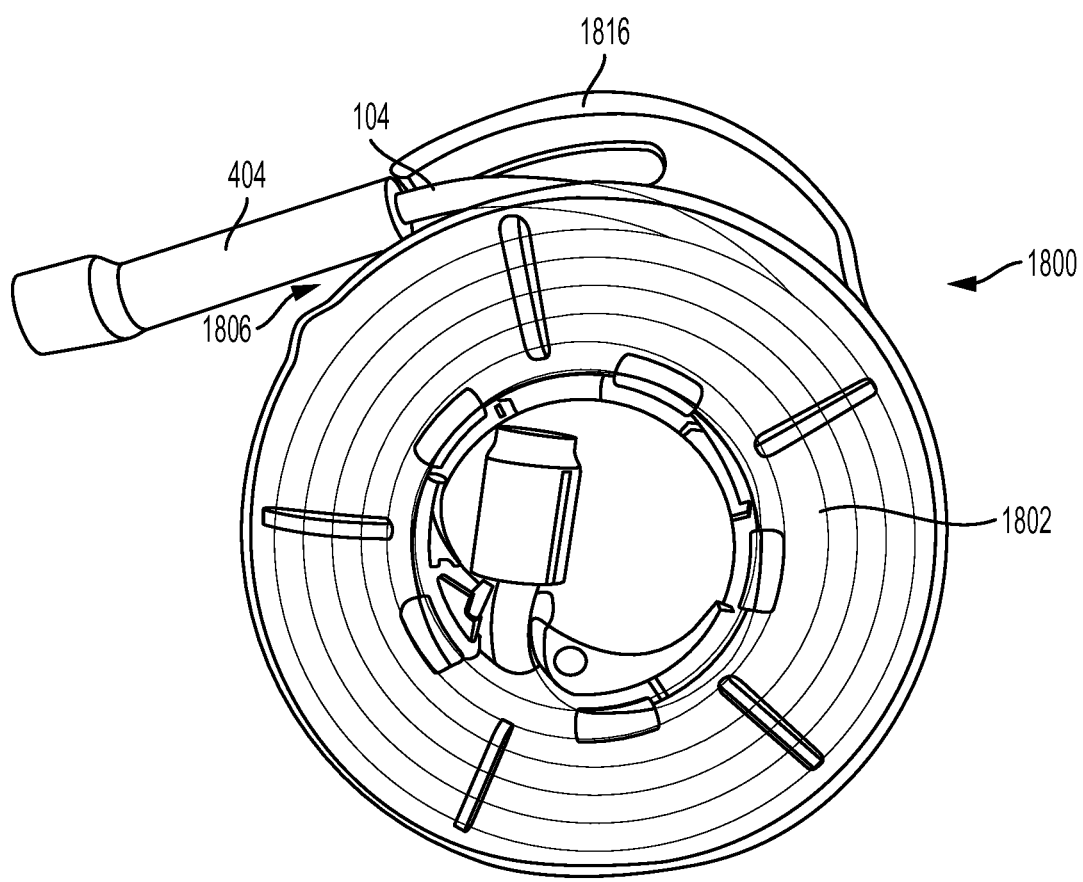

FIG. 18 shows a conceptual drawing of a urinary catheter and enclosure system.

Figure 19A:
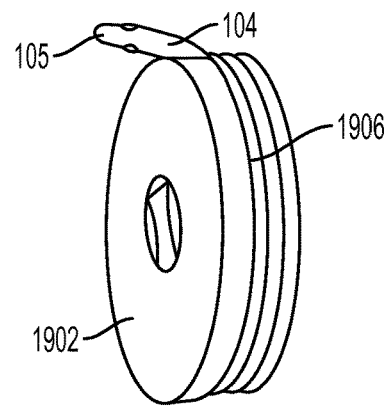
Figure 19B:
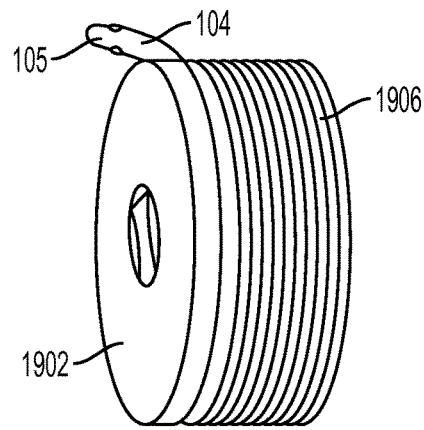
Figure 19C:
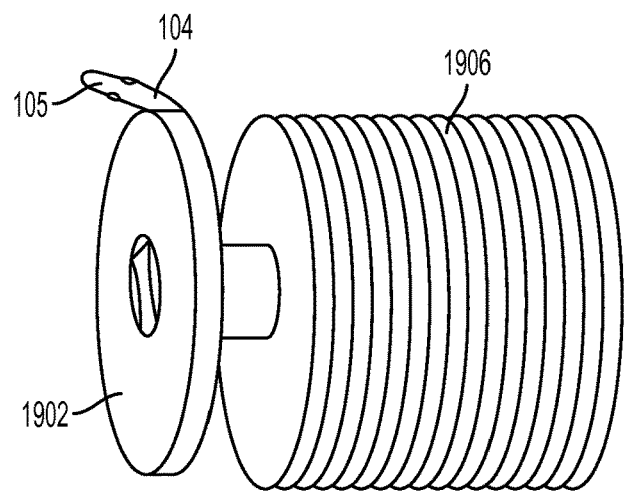

FIGS. 19A-19C show conceptual drawings of catheter attached to a urinary drainage bag.

Figure 20:
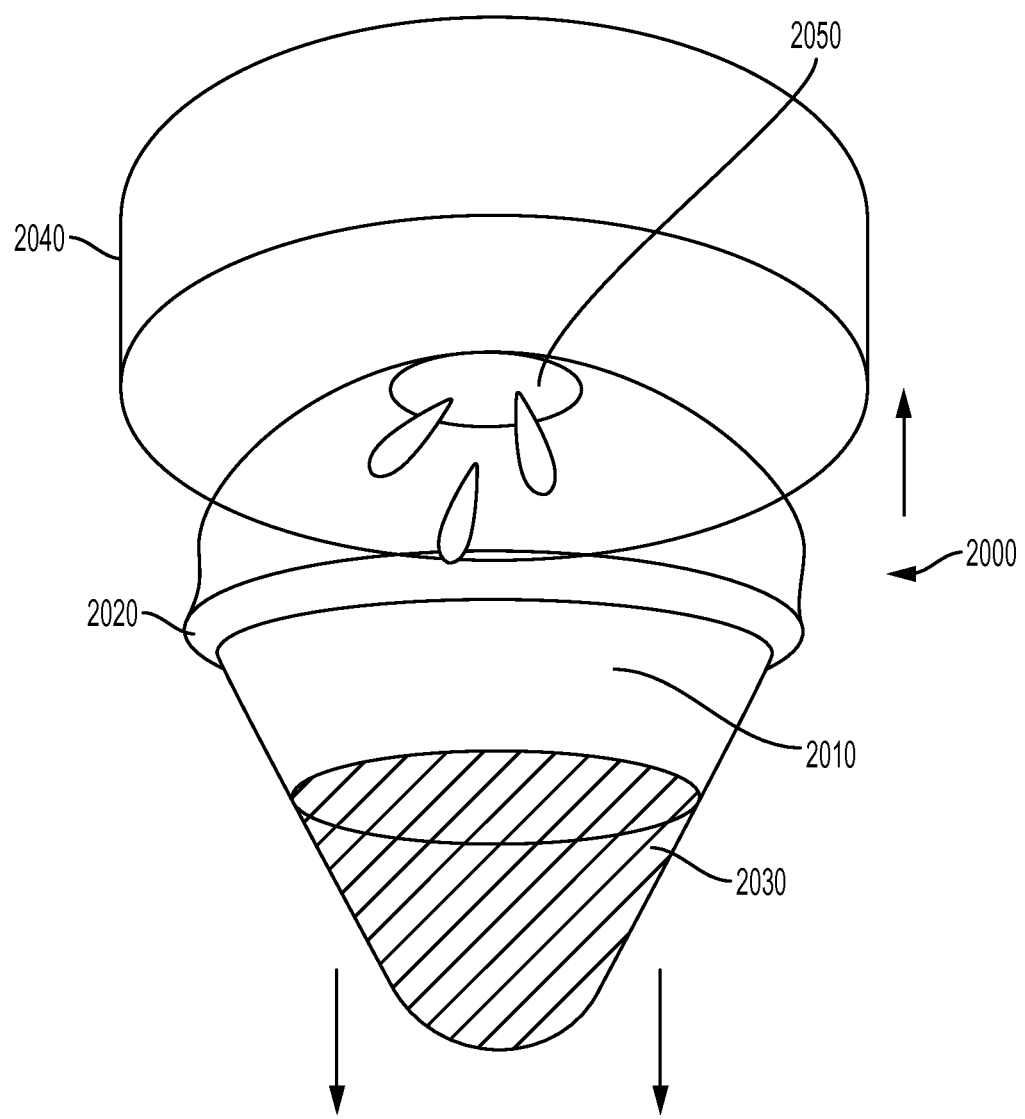

FIG. 20 shows a conceptual drawing of a substance collection apparatus.

Figure 21:
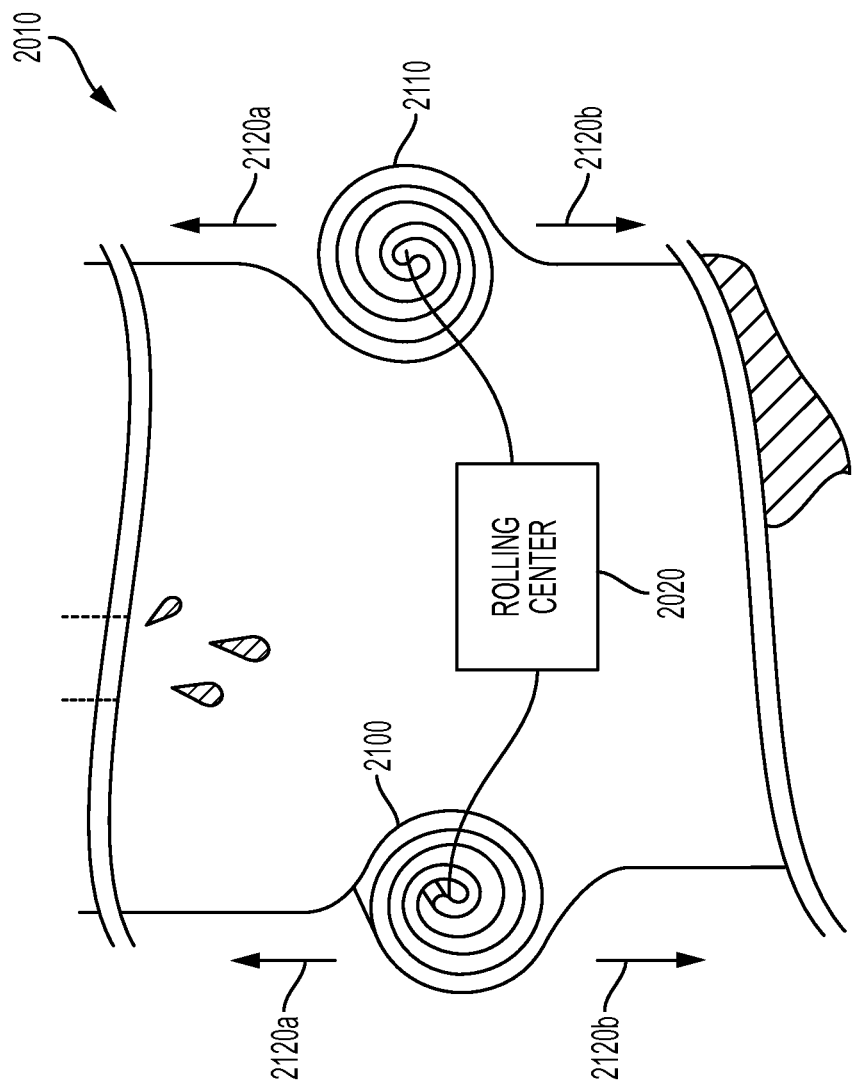

FIG. 21 shows a method of rolling and expanding a special rolling plastic bag.

Figure 22:
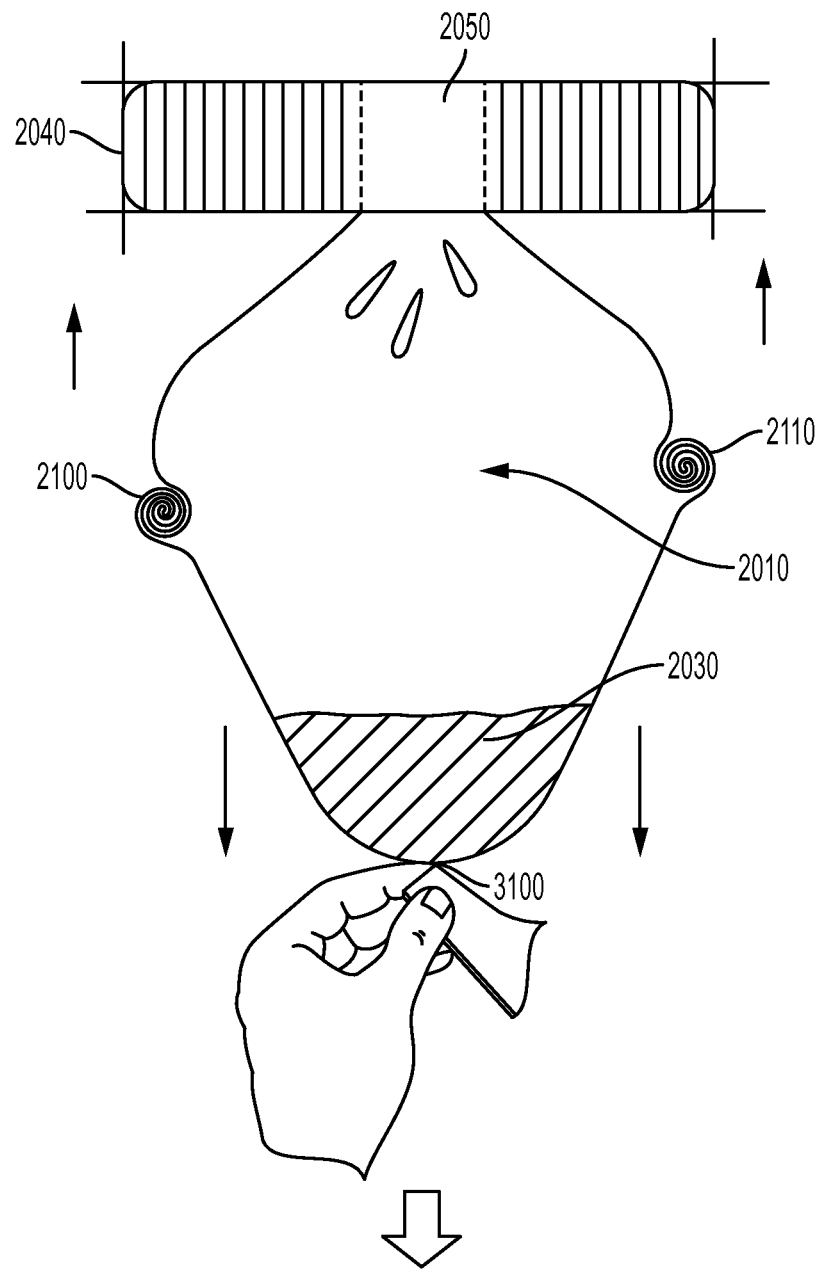

FIG. 22 shows a conceptual drawing of a perspective view of a substance collection apparatus.

DETAILED DESCRIPTION

Compact catheter systems described herein generally include a disposable urinary catheter and a packaging device for the catheter, which work together to provide a more portable, easy-to-use, unobtrusive urinary catheter solution compared to currently available catheters and packaging. In some embodiments, the compact catheter system may include a catheter, packaging and optionally one or more other components, such as one or more lubricants, wipes, urinary collection bag or the like. In other embodiments, the system may include only a catheter and a package. In yet other embodiments, the system may include only a packaging unit and not a catheter, in which case, for example the packaging unit may be used with one of a number of available catheters. Therefore, although the phrase "compact catheter system" is used herein to describe various embodiments, this phrase should not be interpreted as limiting the system to a specific combination of components, devices or the like.

This application describes embodiments of a urinary catheter system that provide users with discreet, hygienic, easy to use access to disposable urinary catheters. In some of the embodiments, the urinary catheter systems are so small, users can typically carry around multiple urinary catheters discretely and comfortably in a purse, backpack, briefcase or even pockets of clothing, without the inconvenience, bulkiness and hygiene risks associated with most currently available urinary catheters.

Unlike currently available urinary catheter packaging, some of the embodiments described herein include packaging that remains attached to the disposable urinary catheter during use. In use, the free end of the catheter is inserted into the urethra (using the sheath to avoid touching the catheter), and the opposite end of the catheter remains in the packaging. When the user voids, urine passes through the opposite end of the catheter, the packaging and then into the toilet or other collection receptacle.

To avoid kinking in the catheter tube that might hinder the flow, one embodiment may include a kink prevention mechanism. This mechanism can be achieved by using a bended funnel in 90° or more in order to create a strain relief for the catheter tube, or by creating a strain relief within the housing.

To prevent leakage or flow of urine before the user is ready to aim to an appropriate receptacle, some embodiments may include a plug that connects to the proximal end of the catheter and prevents urine from flowing until the user releases the plug proximal end from the plug.

Sealed Package

Figure 1A:
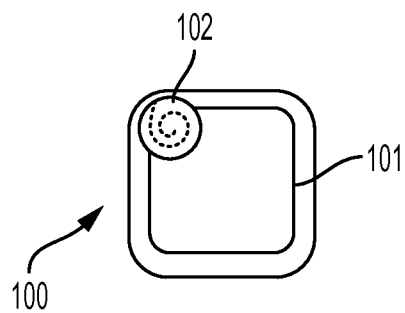
FIG. 1A shows a conceptual drawing of a sealed package capable of holding a compact catheter assembly.
Figure 1B:
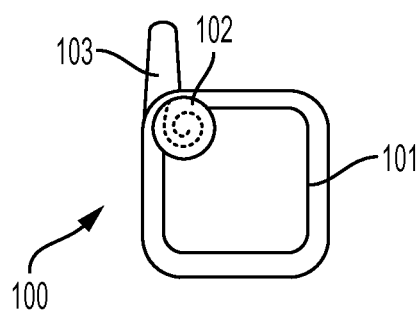
FIG. 1B shows a conceptual drawing of an opened package with a hygienic sheath.
Figure 1C:
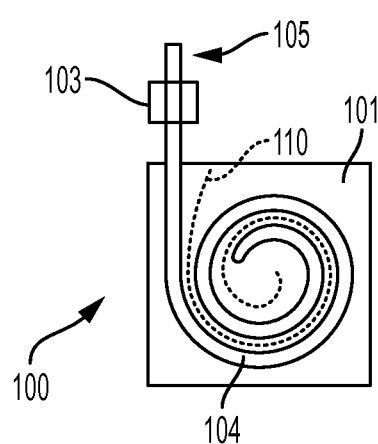
FIG. 1C shows a conceptual drawing of an opened package with a portion of a catheter.

FIGS. 1A-1C show conceptual drawings of a sealed package capable of holding a compact catheter assembly.

FIG. 1A shows a conceptual drawing of a closed package. FIG. 1B shows a conceptual drawing of an opened package with an hygienic sheath. FIG. 1C shows a conceptual drawing of an opened package with an extruded portion of a catheter.

Opening the package. As shown in FIG. 1A, a package 100 includes a sealed enclosure 101, optionally including a breakable, separable, or tearable corner which allows a user to more easily open the package 100 at a designated location.

In one embodiment, the enclosure 101 can be made of foil, glassine, plastic, or some other substance, such as a substance which is relatively opaque (so that urinary patients can be discreet about their use of a urinary catheter), which is at least moderately resistant to breakage or tearing (so that the content of the package 100 remains sterile), and which is relatively susceptible to sterilization (so that the package 100 can be made sterile when constructed).

In one embodiment, a corner where the patch 102 is located is made relatively more susceptible to breakage or tearing than the rest of the enclosure 101, allowing the manufacturer to more easily direct medical personnel where to best open the enclosure 101. In alternative embodiments, the patch 102 is optional. For example, in one example, the corner where the patch 102 is located might be made of paper, such as paper which is glued to the enclosure 101.

While the enclosure 101 is primarily described herein as made of a relatively flexible substance, in the context of the invention, there is no particular requirement for any such limitation. For example, the enclosure 101 may be made of a rigid material, such as a hard plastic, and the patch 102 may be disposed at a specific location intended for exit of the catheter from the package 100.

In such embodiments in which the enclosure 101 may contain a spiral wall made of a rigid material, such as a hard plastic, the catheter can be maintained within the enclosure 101 in a coil or spiral, such as by being disposed within a spiral inner guide-way, such as might be made by a spiral inner wall. In such embodiments, the catheter can still be withdrawn from the package 100, such as by providing a path using the spiral inner wall along which the catheter may be withdrawn from the package 100.

While the package 100 and the enclosure 101 are primarily described herein as being disposed for opening by the urinary catheter patient and withdrawal of the catheter from the package 100 upon opening, in the context of the invention, there is no particular requirement for any such limitation. For example, the package 100 and the enclosure 101 may be disposed in such manner that opening the package 100 causes or prompts an automatic extrusion of a portion the catheter, such as might be caused or prompted by compression or spring-loading of that portion of the catheter.

Hygienic sheath. As shown in FIG. 1B, in one embodiment, the package 100 includes a compact catheter assembly (not shown in this figure), optionally including a hygienic sheath 103, the latter being disposed to cover a distal end 105 of a catheter (not shown in FIG. 1B), the catheter being suitable for insertion in a male or female urethra. In one embodiment, the hygienic sheath 103 can include a first portion which is located at the catheter's distal end and which can be removed, and can include a second portion (not shown in this figure) which can be slidably moved along the catheter, so that the urinary catheter patient can handle the catheter without having to touch the catheter directly.

As described herein, the catheter can be manufactured in one or more sizes, such as relatively distinct lengths or widths. For example, the catheter can be manufactured in a relatively longer or shorter format, for male or female use respectively, or can be manufactured in a relatively narrower or wider format, for pediatric or adult use respectively.

In one embodiment, the hygienic sheath 103 might be made of a relatively flexible material, such as silicone, polyvinyl chloride, or another plastic material. However, in the context of the invention, there is no particular requirement for any such limitation. For example, the hygienic sheath 103 might be made of a form of latex or a latex-free equivalent substance.

As shown in FIG. 1B, the hygienic sheath 103 can be disposed so that it can be handled without exposure of the catheter 104 itself, with the effect that the catheter 104 itself can be maintained sterile even while the catheter 104 is being withdrawn from the package 100. As shown in FIG. 1C, the hygienic sheath 103 can be disposed so that the catheter 104 can include a distal end 105 which is extruded from the hygienic sheath 103 (with the hygienic sheath 103 being disposed to slide along the catheter 104), with the effect that the catheter's distal end 105 can be inserted into the urethra (not shown) while only the hygienic sheath 103 is handled by the patient (or alternatively, medical personnel), with the effect of maintaining the catheter's distal end 105 substantially sterile until it is actually inserted into the urethra.

In one embodiment, the catheter 104 might be made of a relatively flexible material, such as silicone, polyvinyl chloride, or another plastic material. However, in the context of the invention, there is no particular requirement for any such limitation. For example, the catheter 104 might be made of a form of latex or a latex-free equivalent substance.

As described below, in one embodiment, the catheter 104 can be enclosed in the package 100 in a substantially coiled form, with the effect that a relatively elongated catheter 104 can be enclosed within a relatively small package 100. For example, as described in further detail below, the catheter 104 can be enclosed in the package 100 in a coiled form substantially capable of being uncoiled for extension and re-coiled for reinsertion into the package 100.

In one embodiment, the catheter 104, when in the package 100, can be enclosed in a pre-lubricated form, such as by enclosing a lubricant within the package 100 in which the catheter 104 is immersed, or otherwise disposed for lubrication of the catheter 104, such as providing a hydrophilic substance which lubricates the catheter upon application of water. As described below, as the catheter 104 is removed from the package 100, it retains its pre-lubricated form, with the effect that the urinary catheter patient need not expend significant additional effort in either (A) lubricating a catheter 104, or (B) working with an otherwise slippery catheter 104 due to use of the hygienic sheath.

In one embodiment, the catheter 104, when in the package 100, can be maintained in a non-lubricated state, and lubricated by the urinary catheter patient before opening or during opening of the package 100. For example, the catheter 104 can be maintained coated with a hydrophilic lubricant, and coupled to a pouch including water. The patient would be able to press or squeeze the pouch to deliver water to the hydrophilic lubricant, with the effect of lubricating the catheter 104, or the package 100 could be made so that water can be delivered to the hydrophilic lubricant after opening the packaging, or with an alternative water source, or the package 100 can include a hydrophilic lubricant and a water source, or another lubricant.

In embodiments in which the catheter 104 is enclosed in a pre-lubricated form when in the package 100, the package 100 (or the enclosure 101) can include one or more drainage elements, such as gauze or holes, with the effect that the urinary catheter patient can remove any extra lubrication remaining in the package 100 (or the enclosure 101), or any extra water beyond that used to activate the hydrophilic lubricant, so that the urinary catheter patient can be assured that the package 100 will not leak additional lubrication, or additional water, onto unintended locations once the catheter 104 has been removed from the package 100 (whether or not yet inserted into the urethra).

The catheter 104 also includes a proximal end 106 (not shown in this figure). As described, in one embodiment, the proximal end 106 can be used by the urinary catheter patient for voiding urine into an appropriate receptacle, such as a public toilet, without the additional necessity for detaching the catheter 104 from a urinary receptacle, such as a urinary receiving bag or other medical equipment.

In one embodiment, the package 100 can optionally include one or more sanitary wipes 107 (not shown in this figure) or other similarly suited material, with the effect that medical personnel can maintain the catheter 104, the catheter's distal end 105, or the catheter's proximal end 106, substantially sterile even in the event of a mishap, or alternatively, to be used to sterilize the patient's hand before use. As described above, for example, the package of sanitary wipes 107 can be incorporated into the package 100, or otherwise attached in package 100, (A) on a back of the compact catheter assembly, (B) in or near a central hole defined by the compact catheter assembly, (C) attached to a coiled flexible tube, as described below, or (D) at another location convenient for use by the urinary catheter patient.

Spiral internal structure. As shown in FIG. 1C, in alternative embodiments, a spiral internal structure 110 (shown as dotted lines), such as a vertical wall, can be disposed to guide the catheter 104 into a spiral shape, with the effect that a portion of the catheter 104 can be maintained in the enclosure 101 in a spiral form while the rest of the catheter 104 remains in the enclosure 101.

Flexible Tubing

Figure 2A:
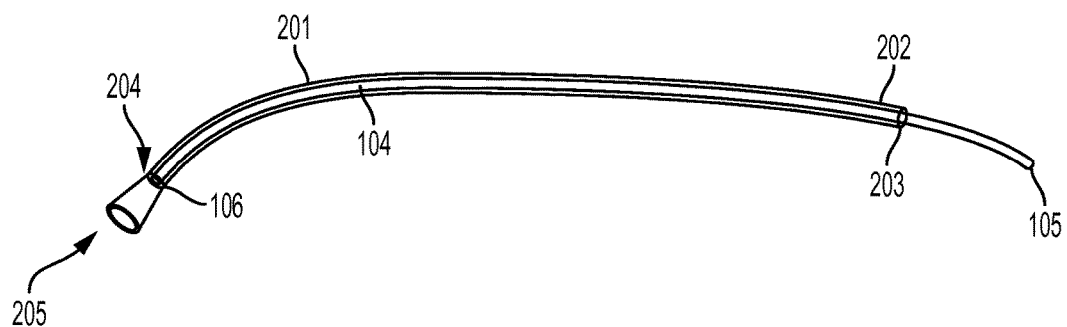
FIG. 2A shows a conceptual drawing of a catheter enclosed in an uncoiled flexible tubing.
Figure 2B:
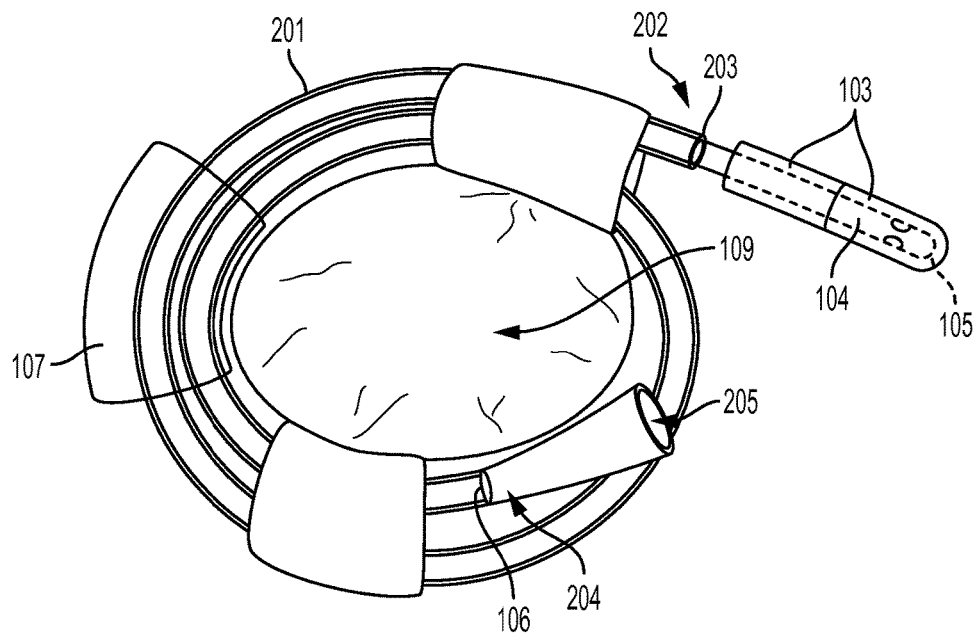
FIG. 2B shows a conceptual drawing of a catheter enclosed in a coiled flexible tubin.

FIGS. 2A and 2B show conceptual drawings of a catheter enclosed in a flexible tubing.

FIG. 2A, show a catheter enclosed in an uncoiled flexible tubing, and a FIG. 2B shows a catheter enclosed in a coiled flexible tubing.

As shown in the panel FIG. 2A and in FIG. 2B, a flexible tubing 201 encloses the catheter 104, with the effect that the catheter 104 is made relatively resilient to breakage or other damage, and with the effect that the catheter 104 can be bent or flexed in response to bending or flexing of the flexible tubing 201.

In one embodiment, the flexible tubing 201 might be made of a relatively flexible material, such as silicone, polyvinyl chloride, or another plastic material. However, in the context of the invention, there is no particular requirement for any such limitation. For example, the flexible tubing 201 might be made of a form of latex or a latex-free equivalent substance.

In one embodiment, the flexible tubing 201 includes a distal tubing end 202, defining a distal tubing hole 203. In one example, the catheter's distal end 105 can be pushed through the distal tubing hole 203, with the effect that the catheter's distal end 105 can be directly inserted into the urethra.

As described above, in one embodiment, the hygienic sheath 103 can include a first portion (shown as "removable end") which is located at the catheter distal end 105 and which can be removed, and can include a second portion (shown as "slidable portion") which can be slidably moved along the catheter. In such embodiments, the hygienic sheath 103 can be disposed so as to be separable from the distal tubing end 202.

In one embodiment, the flexible tubing 201 includes a proximal tubing end 204, defining a proximal tubing hole 205. In one embodiment, the proximal tubing hole 205 can be relatively wider than the main portion of the flexible tubing 201, with the effect that the proximal tubing hole 205 is relatively well suited for coupling to a receptacle (not shown in this figure) for urine to be voided.

Similar to the distal tubing end 202, in one embodiment, the proximal tubing end 204 can have a secondary sheath (not shown) which can be removed from the proximal tubing end 204, allowing exit of fluids such as urine from the proximal tubing hole 205. Having both the distal tubing end 202 and the proximal tubing end 204 covered has the effect that the inside of the flexible tubing 201 is sealed against air and any consequent contact with infectious elements.

In one embodiment, as described herein, urine is coupled from the urethra, through the catheter's distal end 105 and the distal tubing hole 203, through the main portion of the catheter 104, to the catheter's proximal end 106 and the proximal tubing hole 205, to one or more receptacles. For a first example, the receptacles can include a urine bag or other sanitary holding element. For a second example, the receptacles can include a flush toilet or other suitable sanitary element for removing urine.

As shown in FIG. 2B, the flexible tubing 201 can be disposed in a coiled or helical shape, with the effect that it takes relatively little space. For example, the flexible tubing 201, in its coiled or helical shape, can be fit into the package 100, which might look much like a package including a condom, with the effect that the presence of the catheter 104 with the urinary catheter patient can be made relatively convenient and discreet.

The hygienic sheath 103 can be disposed in two parts: a first portion which covers the catheter distal end 105, and which can be discarded, and a second portion which can be slidably moved along the catheter 104, such as after the catheter 104 has been lubricated, and which can be used by the urinary catheter patient to hold the catheter 104 without directly touching it.

In one embodiment, the coiled flexible tubing 201 can have one or more sanitary wipes 107 coupled thereto, with the effect that the sanitary wipes 107 are conveniently available to the urinary catheter patient when using the catheter 104.

In one embodiment, the coiled flexible tubing 201 can have a water pouch 109 or a pouch including a lubricant coupled thereto, and disposed so that when the urinary catheter patient presses or squeezes the water pouch 109, water is pressed or squeezed out of the water pouch 109 and into the flexible tubing 201 and onto the catheter 104. The water pouch 109 can be disposed in a position so that water is pressed or squeezed out even when the water pouch 109 is inside an unopened package 100. This has the effect that the patient can lubricate the catheter 104 relatively easily, even when the catheter 104 is still inside an unopened package 100, with the effect that the patient can have the catheter 104 ready and prepared for convenient and discreet use.

Construction of tubing. In one embodiment, the catheter 104 is manufactured within the flexible tubing 201 using a sequence of steps:

In a first step, the catheter 104 can be placed within the flexible tubing 201.

In a second step, the catheter 104 inside the flexible tubing 201 can be turned into a flexible spiral structure, and fixed, such as with heat or solvent.

In a third step, the catheter 104 inside the flexible tubing 201 can be placed into a condom-like enclosure 101.

In a fourth step, a distal end of the flexible tubing 201 can be detached, with the effect that the detached portion can serve as a sliding sheath for the catheter 104.

In a fifth step, one or more central portions of the flexible tubing 201 can be coupled to a water pouch, with the effect that the water pouch can pump (or exude) water into the flexible tubing 201 before use of the catheter 104. This has the effect that a hydrophilic coating of the catheter 104 can be activated before use of the catheter 104.

In a sixth step, the catheter 104 can be deployed from within the flexible tubing 201 for use.

In alternative embodiments, if the catheter 104 is maintained within the flexible tubing 201 during use of the catheter 104, one or more central portions thereof can serve as outlets for fluid entering the catheter 104.

Catheter Assembly

FIGS. 3A-3E show conceptual drawings of a catheter assembly, including a catheter maintained in a compact form factor.

FIGS. 3A and 3B show conceptual drawings of a bottom element and a top element, respectively, of the catheter assembly FIGS. 3C and 3D show conceptual drawings of the bottom and top elements unassembled and assembled respectively, FIG. 3E shows a conceptual drawing of the catheter uncoiled and attached to the catheter assembly.

Catheter assembly elements. As shown in FIGS. 3A and 3B, a catheter assembly 301 can include a bottom element 310 and a top element 320. The bottom element 310 can include an internal bottom edge 311 and an external bottom edge 312.

Similarly, the top element 320 can include an internal top edge 313 and an external top edge 314. In one embodiment, the internal bottom edge 311 is similarly sized as the internal top edge 313, and is disposed for coupling thereto. Similarly, in one embodiment, the external bottom edge 312 is similarly sized as the external top edge 314, and is disposed for coupling thereto.

In one embodiment, the internal bottom edge 311 and the internal top edge 313 are each substantially circular, and are disposed for rotation about a common axis, with the effect that rotation of the bottom element 310 with respect to the top element 320 allows the internal bottom edge 311 and the internal top edge 313 to move radially, with respect to each other, about that common axis.

Similarly, in such embodiments, the external bottom edge 312 and the external top edge 314 are each substantially circular, and are disposed for rotation about that same common axis, with the effect that rotation of the bottom element 310 with respect to the top element 320 allows the external bottom edge 312 and the external top edge 314 to move radially, with respect to each other, about that common axis.

After reading this application, those skilled in the art will recognize that the bottom element 310 and the top element 320 may move radially with respect to each other by any one of a number of alternatives, each of which would be workable, is within the scope and spirit of the invention, and would not require further invention or undo experiment. For example, the bottom element 310 may move while the top element 320 is relatively stationary, the bottom element 310 may be relatively stationary while the top element 320 may move, or both the bottom element 310 and the top element 320 may move.

In one embodiment, the internal edge 311 includes an internal hole 315, through which the proximal catheter end 106 can be placed. In those embodiments in which the proximal catheter end 106 is relatively wider than the main portion of the catheter 104, the proximal catheter end 106 has the effect of restricting the proximal catheter end 106 from slipping through the internal hole 315, and the effect of anchoring the proximal catheter end 106 at the internal edge 311 of the bottom element 310.

While this application describes an assembly in which the proximal catheter end 106 is flared, and that the flaring of the proximal catheter end 106 has the effect of restricting the proximal catheter end 106 from slipping through the internal hole 315, in the context of the invention, there is no particular requirement for any such limitation. The catheter 104 can be used to void urine, with the flared proximal catheter end 106 having other purposes, such as for aim or otherwise.

In one embodiment, the bottom element's internal edge 311 includes a flexible protruding wall, which can be coupled to the top element 320. In alternative embodiments, the top element's internal edge 313 includes the flexible protruding wall, which can be coupled to the bottom element 310. This has the effect that the bottom element 310 and the top element 320 form a spool-like shape, including a center around which the catheter 104 can be wound.

In one embodiment, the top element's external edge 313 includes a protruding wall, not necessarily coupled or flexible, which can be mated to the bottom element 310. In alternative embodiments, the bottom element's external edge 312 includes a protruding wall, not necessarily coupled or flexible, which can be mated to the top element 320. This has the effect that the bottom element 310 and the top element form a closed spool-like shape, including an external wall within which the catheter 104 can be wound.

Catheter assembly joinder. As shown in FIGS. 3C and 3D (FIG. 3C showing an unattached assembly and FIG. 3D showing an attached assembly), in one embodiment, when the bottom element 310 and the top element 320 are coupled together, they form a donut-shaped space, having a centrally-located internal core wall 331, a peripherally-located external restraining wall 332, a bottom restraining wall 333, and a top restraining wall 334.

In one embodiment, the donut-shaped space is seen to have a substantially circular internal core wall 331, a substantially circular external restraining wall 332, a substantially flat bottom restraining wall 333, and a substantially flat top restraining wall 334. However, in the context of the invention, there is no particular requirement for any such limitation.

For a first example, the substantially circular internal core wall 331 and the substantially circular external restraining wall 332 might each be polygonal in shape, such as one or more of them forming a multi-sided regular polygon.

For a second example, the internal core wall 331 and the external restraining wall 332 might each define one or more additional holes, with the effect of not necessarily defining solid walls.

For a third example, one or more of the bottom restraining wall 333 and the top restraining wall 334 need not be substantially flat; instead one or more of them could define a bulge, an inverse bulge, or some other surface.

For a fourth example, one or more of the bottom restraining wall 333 and the top restraining wall 334 might each define one or more additional holes, with the effect of not necessarily defining solid walls.

The internal core wall 331 could be defined by the joinder of the bottom element's internal edge and the top element's internal edge. The external restraining wall 332 could be defined by a joinder of the bottom element's external edge and the top element's external edge. The bottom restraining wall 333 could be defined by that portion of the bottom element 310 from its internal bottom edge 311 to its external bottom edge 312. The top restraining wall 334 could be defined by that portion of the top element 320 from its internal top edge 313 to its external top edge 314.

After reading this application, those skilled in the art would see that there are other constructions, dispositions, and other alternative structures for the bottom element 310 and the top element 320, that such alternative structures would be workable without further invention or undue experiment, and are within the scope and spirit of the invention.

For a first example, the bottom element 310 could include portions of the structure described herein to be part of the top element 320, or vice versa. Such examples could involve including one or more portions of the internal core wall 331 in the bottom element 310, the top element 320, shared between the bottom element 310 and the top element 320, or otherwise assigned in parts among the bottom element 310 and the top element 320.

For a second example, the structures described herein could be divided otherwise than a bottom element 310 and a top element 320, or could include more than two such elements, or could include elements which are mated together at different locations or in different ways.

In one embodiment, the catheter 104 and the flexible tubing 201 are disposed within the donut-shaped space, in such manner as to form a substantially flat spiral, such as shown in FIG. 3D. However, in the context of the invention, there is no particular requirement for any such limitation.

For a first example, there is no particular requirement that the spiral is substantially flat.

For a second example, the catheter 104 might be disposed within the donut-shaped space in such manner as to form a helix or other coil 340, with the effect that the catheter 104 can be wound in parallel or more than once within the donut-shaped space.

In one embodiment, the catheter 104 is disposed with the distal tubing hole 203 being placed through the external hole 316, with the effect that the catheter 104 can be drawn out from the catheter assembly 301. This would have the effect that the catheter 104 would be uncoiled as it is drawn out from the catheter assembly 301, reducing the portion of the catheter 104 remaining within the catheter assembly 301.

In one embodiment, the catheter 104 is disposed with the proximal catheter end 106 being placed through the internal hole 315, with at least two effects. First, the proximal catheter end 106 is substantially anchored by its placement at the internal hole 315, with the effect that the catheter 104 is relatively resistant to being pulled completely out of the catheter assembly 301. Second, the proximal catheter end 106 is substantially available at a location external to the catheter assembly 301, with the effect that the catheter 104 can convey liquids from the distal catheter end 105 to the proximal catheter end 106, so that urine can be voided from the urethra into an appropriate receptacle, such as a public toilet, or alternatively into a urinary receiving bag or other medical equipment.

In one embodiment, the bottom element 310 and the top element 320 move radially with respect to each other when the catheter 104 is extended from the catheter assembly 301.

Similarly, the bottom element 310 and the top element 320 can be disposed to move radially in an opposite direction, with the effect that the catheter 104 is retracted into the catheter assembly 301, with one or more effects. For example, the catheter's distal end 105 can be retracted to a point where it is withdrawn inside the catheter assembly 301, and the catheter assembly 301 repackaged, such as for disposal.

In one embodiment, the bottom element 310, the top element 320, or both, can include bumps, handles, ridges, or other elements, suitable for the urinary catheter patient to easily move the bottom element 310 radially with respect to the top element 320.

For a first example, the bottom element 310, the top element 320, or both, can include radially disposed ridges, with the effect that the urinary catheter patient can move the bottom element 310 radially with respect to the top element 320 using their fingers and winding one or more of the bottom element 310 and the top element 320 about their common axis.

For a second example, the bottom element 310, the top element 320, or both, can include ridges disposed on at least a portion of the external restraining wall 332, with the effect that the urinary catheter patient can move the bottom element 300 and radially with respect to the top element 320 using their fingers and winding one or more of the bottom element 310 and the top element 320 about their common axis.

Catheter attachment to assembly. As shown in FIG. 3E, the catheter 104 is coupled at the first point described with respect to FIGS. 3A and 3B and the second point described with respect to FIGS. 3C and 3D.

As described above, the catheter 104 is placed through the external hole 316, with the effect that the catheter 104 can be drawn out from the catheter assembly 301. In FIG. 3E, the catheter 104 is shown already drawn out from the catheter assembly 301, so as to form a relatively straight-line element, such as might occur during use.

As also described above, the catheter 104 is disposed with the proximal catheter end 106 being placed through the internal hole 315, with the proximal catheter end 106 being substantially anchored by its placement at the internal hole 315. In FIG. 3E, the catheter 104 is shown with the proximal catheter end 106 already substantially anchored by its placement at the internal hole 315, such as might occur during use.

After reading this application, those skilled in the art would recognize that this particular disposition of the assembly as described is not absolutely required, and that many variants thereof would be workable and would be within the scope and spirit of the invention, and would not require further invention or undue experiment.

Enclosure with Pinchable Handle

FIG. 4 shows another embodiment of a urinary catheter and enclosure system 400. The system 400 includes a urinary catheter 104, a majority of which is housed in an enclosure 402. The catheter 104 has a distal end 105 configured for insertion into a urethra and a proximal end 106. A funnel 418 may be disposed at the proximal end 106 of the catheter 104. A hygienic sheath 404 is disposed on a portion of the catheter 104 near its distal end 105. The distal end 105 of the catheter 104 may extend out of the enclosure 402 through an outer hole 406, which may be defined by an outer peripheral wall 430 of the enclosure 402. The proximal end 106 of the catheter 104 may extend out of the enclosure 402 through an inner hole 408, which may be defined by an inner peripheral wall 432 of the enclosure 402. Thus, the enclosure 402 may have a donut shaped configuration, within which the catheter 104 may wind.

The sheath 404 is slidable by a user along the catheter 104. For example, the user may use the sheath 404 to pull the catheter 104 out of the enclosure 402 through the outer hole 406, and then may slide the sheath 404 proximally along the catheter 104 from a first position, shown in FIG. 4, to a second, more proximal position. The sheath 404 in the second position will expose the distal end/distal portion of the catheter 104, for example to allow a user to insert the distal end 105 of the catheter 104 into the urethra. After advancing the distal end 105 into the urethra, the user may then slide the sheath 404 proximally along the catheter 104 again, to a third position, pull the catheter 104 farther out of the enclosure 402, and advance the catheter 104 farther into the urethra. This process may be repeated as many times as necessary to advance the distal end 105 of the catheter 104 into the bladder. In performing this catheter advancing method, there need not be (and typically will not be) any predefined "first position," "second position" and so on of the sheath 404 relative to the catheter 104. Instead, the sheath 404 may be moved proximally and used to advance the catheter 104 in any convenient fashion by the user. In general, the slidable sheath 404 allows a user to advance the catheter 104 out of the enclosure and into the urethra without touching the catheter 104, thus reducing the risk of infection.

As will be described in further detail below, the enclosure 402 may include a handle portion 416 (or "pinching portion"), which moves inward when pressure is applied to it, typically by a finger of the user. FIG. 4 shows a user's finger 420 pinching the handle portion 416 radially inward, thus pinching the catheter 104 and restricting movement of the catheter 104 through the outer hole 406. Thus, the handle portion 416 holds the catheter 104 in place while the user slides the sheath 404 back (proximally) along the catheter body, thus preventing the proximal movement of the sheath 404 from inadvertently pushing the catheter 104 back into the enclosure 402. When the user releases the inward pressure from the handle portion 416, the handle portion 416 will move (or spring) outward to its default position, thus freeing the catheter 104 to move through the outer hole 406.

In some embodiments, the internal diameter of the catheter 104 may get smaller as it coils into the enclosure. This design prevents the catheter 104 from pulling all the way into the enclosure 402. As the catheter 104 coils in, it starts coiling tighter and tighter, until it fills the allotted internal case space and leaves the distal part with the sheath 404 outside of the enclosure 402.

FIG. 5A shows an assembled enclosure 502, including a bottom member 510 and a top member 512, according to one embodiment. FIG. 5B shows the top member 512 disassembled from the bottom member 510. The top member 512 forms at least a portion of an outer peripheral wall 520 of the enclosure 502. The enclosure 502 may have an outer peripheral wall 520 and an inner peripheral wall 524, and the enclosure 502 can have a donut shaped configuration, within which the catheter 104 may wind. The outer peripheral wall 520 includes a handle portion 516. When a user applies handheld pressure to the handle portion 516, the handle portion 516 moves radially inward, into the cavity of the enclosure 502. Thus, upon a user applying handheld pressure to the handle portion 516 (e.g., pinching the enclosure 502), the handle portion 516 pinches the catheter 104 and restricts movement of the catheter 104 through the outer hole 506. In the embodiment shown in FIGS. 5A and 5B, the handle portion 516 is formed by a cutout portion 518 in the top member 512.

Plug

In some embodiments, the catheter system may include a plug that is insertable into the proximal end 106 of the catheter 104 to prevent fluid flow therethrough.

Plug that is part of the enclosure. FIGS. 6A-6C show, respectively, a bottom member 610, a top member 612, and an assembled enclosure 602 comprising a bottom member 610 and top member 612, according to one embodiment. As shown, the bottom member 610 can include a cut-out portion that defines the inner hole 608. A plug 622 is disposed on the inner peripheral wall 624 of the enclosure 602. The plug 622 can be disposed across from the inner hole 608, so that the proximal end 106 of the catheter 104 (not shown in FIGS. 6A-6C) can extend out of the inner hole 608 to engage the plug 622, so that urine is prevented from flowing out of the proximal end 106.

The plug 622 provides the user with a more calm and controlled catheterization process. Using currently available self-catheterization devices, the user inserts a catheter into their urethra and into the bladder. The moment the catheter reaches the bladder, urine starts to flow instantaneously out of the proximal end of the catheter. If the user is not prepared and has not aimed the proximal end of the catheter into an appropriate receptacle, the urine will flow onto the user's clothes, the floor of the bathroom, etc. In the current embodiment, the plug 622 prevents the urine from flowing until the user is ready and has directed the proximal end 106 of the catheter 104 toward/into an appropriate receptacle.

In operation, while the user pulls the catheter 104 out of the enclosure 602 and inserts the distal end 105 into the urethra, the catheter proximal end 106 stays engaged with the plug 622. Once the catheter 104 is fully inserted, the user can pull the proximal end 106 of the catheter 104 from the plug 622 and direct it towards an appropriate receptacle (such as a toilet bowl) and drain the bladder. The plug 622 may work with a catheter 104 with or without a funnel at the proximal end (e.g., a funnel 418 as shown in FIG. 4).

FIGS. 7A and 7B show a bottom member 710 of an enclosure, according to one embodiment. The bottom member includes an inner peripheral wall 724 and a plug 722. An inner hole 708 is defined by the bottom member 710. In this embodiment, the plug 722 is simply taller/longer than the plug 622 described above.

FIG. 8 shows a bottom member 810 of an enclosure and a catheter 104, according to one embodiment. The bottom member 810 includes an inner peripheral wall 824 defining an inner hole 808, through which the catheter 104 extends. Across from the inner hole 808, on the inner peripheral wall 824 is a plug 822. FIG. 8 shows the catheter 104 engaged with the plug (the plug 822 is inserted into the proximal end 106 of the catheter 104 to prevent fluid flow therethrough). In the embodiment shown in FIG. 8, the inner hole 808 is located approximately directly across from the plug 822, so that the proximal end portion of the catheter 104 can extend generally linearly from the inner hole 808 to engage the plug 822.

Detached Plug. FIGS. 9A-9C show another embodiment of a plug 904 that prevents urine from coming out of the proximal end 106 of the catheter 104. In this embodiment, the proximal end 106 of the catheter 104 includes a funnel 902, and the plug 904 is engageable with the funnel 902. FIGS. 9A-9C show a plug 904 that is hingedly connected to a funnel 902 via a connecting portion 906, to form an assembly 900. In other embodiments, the plug 904 may be separate from the funnel 902. In operation, when the user is ready, the user can pinch the proximal end 106 of the catheter 104 to disengage the plug 904 from the funnel 902 and/or pull the plug 904 out of the funnel 902 with the fingers. In some embodiments, the plug 904 and/or funnel 902 may be made of a water soluble material, so that it can be flushed down the toilet.

Living Hinge Housing

FIGS. 10A and 10B show a urinary catheter and enclosure system 1000 according to one embodiment. The enclosure 1002 includes a handle portion 1016 that is hingedly engaged with the outer peripheral wall 1026 of the enclosure. When the handle portion 1016 is moved radially outward, the catheter 104 may extend out of the outer hole 1006.

In operating the urinary catheter and enclosure system 1000, the user may open an outer package/pouch (not shown here but described above), for example by tearing open a perforated edge of the outer package, and remove the catheter enclosure 1002 from the outer package. The catheter enclosure 1002 includes two interlocking members (e.g., top member 1012 and bottom member 1010) that can rotate around each other while remaining interlocked, which allows the catheter 104 to be deployed or retracted. When the user pulls the enclosure 1002 out, all or most of the catheter 104 (aside from the funnel 1402) may be contained in the enclosure 1002. The user can then pop up the hingedly attached handle portion 1016. The distal end 105 of the catheter 104 pops out of the enclosure 1002 as it assumes its original straight shape. The user then uses the hygienic sheath (not pictured) to pull out the catheter 104 and insert it into the urethra or a stoma. The catheter 104 stays in the enclosure 1002 as the user gradually pulls it out and inserts it into the urethra and through the urinary sphincter. Once the distal end 105 of the catheter 104 is inside the bladder, urine flows through the catheter 104 and the funnel 1402 protruding from the interior hole 1008 of the enclosure 1002. (In some embodiments, a plug may be used with the funnel 1402, as discussed above, to allow the timing of bladder voiding to be further controlled.) After use, the user can easily retract the catheter 104 into the enclosure 1002 by twisting the enclosure 1002 until the catheter 104 is coiled back in. Then, the user can return the enclosure 1002 containing the catheter 104 to its outer package.

When the hinged handle portion 1016 is closed, it locks together the top member 1012 and bottom member 1010 that make up the enclosure 1002 in a way that prevents them from spinning and from the catheter 104 being pulled back in. This may be achieved by any suitable locking means, such as but not limited to a pin on one of the two members fitting into a curved portion of the other of the two members. The enclosure 1002 is designed in such way that its internal circle (the one the funnel comes out of) has several holes of different sizes to accommodate different catheter diameters.

Tape

Referring now to FIG. 11, in another embodiment a urinary catheter and enclosure system 1100 may include an outer peripheral wall 1126 of an enclosure 1102, which defines an outer hole 1106 through which the distal end 106 of the catheter 104 can extend. Prior to use, a piece of tape 1130 covers the outer hole 1106 to protect the catheter 104 contained within the enclosure 1102. When a user is ready to use the catheter 104, the user removes the tape 1130 to expose the distal end 105 of the catheter, which may have a sheath 404. The user can then grab the sheath covered distal end 105 and use the catheter 104 as described above.

Different Sheath Shapes

FIGS. 12A-12F show embodiments of urinary catheter and enclosure systems 1200(a)-1200(f). FIGS. 12A-12F show systems 1200(a)-1200(f) having enclosures 1202 of a similar design, but that have different embodiments of hygienic sheaths 1204, 1206, 1208, 1210, 1212, 1214. In some embodiments, the hygienic sheaths 1204, 1206, 1208, 1210, 1212, 1214 may have a length about equal to (e.g., equal to) 1.5 inches, although in alternative embodiments they may have any of a number of other suitable lengths. The various different shapes and configurations illustrated may be advantageous for gripping the sheaths 1204, 1206, 1208, 1210, 1212, 1214 and sliding them along a catheter.

Grip Handles

Referring now to FIG. 13, the urinary catheter and enclosure system 1300 may include a gripping feature 1313 (or multiple features) to help provide easy, intuitive and ergonomic gripping, indicating the right grip by providing designated space(s) for a thumb and/or fingers of a user's hand. The gripping feature 1313 may be a recessed groove or an indentation on the outer peripheral wall 1330 of the enclosure 1302.

Bended Catheter Funnel

FIG. 14 shows portions of two catheters 104 near their proximal ends 106. As shown, a funnel 1402 may be attached to the proximal end 106 of the catheter 104. The catheter 104 may be coiled in a spiral shape, and the funnel 1402 may have a bent configuration in order to create a strain relief for the catheter 104 and avoid kinks in the catheter 104. In one embodiment, the bend in the funnel 1402 may have an angle of 90° or approximately 90°. The strain relief created by the bent funnel 1402 may reduce or eliminate kinking of the catheter 104 as the catheter 104 moves and bends. Thus, the bent funnel 1402 allows flexibility in the catheter 104 without putting stress on the vulnerable point near the proximal end 106, where the 104 needs to bend. This funnel 1402 configuration is also shown in FIGS. 10A and 10B.

Closed System

With reference now to FIGS. 15A-15C, in some embodiments of a urinary catheter and enclosure system 1500, the catheter's enclosure 1502 may be made of two components 1501, 1503. The first component 1501 may have an outer peripheral wall 1530 that defines an outer hole 1506. A top portion 1516 may hingedly move between a closed configuration, in which it forms a part of the peripheral wall 1530 of the enclosure 1502 (FIG. 15B), and an open configuration to expose an outer hole 1506 (FIGS. 15A and 15C), through which the distal end of a catheter may extend. The first component 1501 may have three living hinges. The second component 1503 may be a disk that connects to the inner periphery of the first component 1501 with a living hinge. A user can move the second component 1503 relative to the first component 1501 in order to coil the catheter (not shown) out of or back into the enclosure 1502. For example, a user may grasp handle portion 1504 (or any other portion of the second component 1503) to rotate the second component 1503 relative to the first component 1501, to thereby cause the catheter to wind into and out of the enclosure 1502.

Deployment Method

FIGS. 16A-C show an embodiment of a urinary catheter and enclosure system 1600. The enclosure 1602 has an outer peripheral wall 1630 that defines an outer hole 1606. A top portion 1616 is hingedly attached so that it may move between a closed configuration, in which it forms a part of the peripheral wall 1603, and an open configuration to expose an outer hole 1606 (as shown in FIG. 16A), through which the distal end of a catheter may extend. The enclosure 1602 may have an inner peripheral wall 1632. A handle 1603 is hingedly engaged to the enclosure 1602 via a living hinge. The handle 1603 can move between a closed configuration, in which it at least partially covers the peripheral wall 1632 (FIG. 16B), and an open configuration (FIGS. 16A and 16C). When the handle 1603 is in the open configuration, a user can grasp the handle 1603 (e.g., by grasping a knob on the handle) to turn the enclosure 1602 and retrieve the catheter after use. For example, a user may grasp handle portion 1603 to rotate the one component 1601 of the enclosure 1602 relative to another component of the enclosure 1602, to thereby cause the catheter to wind into and out of the enclosure 1602.

Case with a Hood

FIG. 17 shows an embodiment of a urinary catheter and enclosure system 1700. The enclosure 1702 may include a hood 1716 that extends over the outer hole 1706 of the enclosure 1702 in order to protect the catheter 104. The hood 1716 also guides the catheter 104 so that the catheter 104 maintains a spiral shape as it is unwound from the enclosure 1702. The hood 1716 also guides the catheter 104 to extend out of the outer hole 1716 parallel to the enclosure 1702 and maintain a "square" frame.

Pinching Handle

FIG. 18 shows an embodiment of a urinary catheter and enclosure system 1800. The enclosure 1802 includes a handle portion 1816 that can flex radially inward, to pinch the catheter 104, and thus prevent the catheter 104 from moving into or out of the outer hole 1806. The handle 1816 is configured to hold the catheter 104 in place while the user slides the sheath 404 relative to the catheter 104, so to prevent the catheter 104 from coiling back into the enclosure 1802.

Compact Catheter with a Urinary Drainage Bag

With reference now to FIGS. 19A-C, the catheter 104 may be coiled in a spiral shape, and the catheter 104 may have a funnel (not shown) attached to a urinary drainage bag 1906. As seen in FIG. 19A, the bag 1906 can be folded so that it remains rather flat close to the surface of the case. It may be folded in an accordion or a similar compact form. The bag 1906 is placed in the backside of an enclosure 1902. When the patient pulls the enclosure 1902 out of its packaging (packaging not seen in figure), the patient can grab the bag 1906 in the perforated edge, pulling it outward direction and by that, unfolding it until it's fully opened, and prepared for use. When the patient then uses the catheter 104 (as described in previous embodiments), the urine drains into the urine bag 1906. When the patient is done, the patient can tear the tip of the perforated edge of the bag 1906 and drain the urine from the bag 1906.

In operation, the catheter may be used with the following insertion method where the catheter case is used as a handle and gives resistance to make insertion easier. In this method, the patient pulls out the distal end of the catheter by using the sliding sheath. The patient then pulls out about 2" of the catheter out while sliding the sheath away from the distal end and towards the enclosure, applying lubricant on the way. The patient then holds the organ in one hand and the enclosure in the other hand. Holding the enclosure as a handle, the patient then inserts the catheter into the organ and once the distal end of the catheter is inserted, the patient grabs the sheath with the hand that grabs the organ. The patient then turns the enclosure so that the funnel is facing towards the toilet bowl or urinal and continues inserting the catheter, releasing the sheath every time s/he wants to push the catheter inside and gripping the sheath whenever s/he needs to release more of the catheter from the case.

Collection Apparatus

FIG. 20 is a perspective view of a substance collection apparatus 2000. As illustrated in FIG. 20, the substance collection apparatus 2000 can include a special rolling plastic bag 2010 and a portably functional receptacle 2040. The special rolling plastic bag 2010 may be made from many kinds of polymers such as polyethylene (PE), polypropylene (PP), polyvinyl chloride (PVC), ethylene vinyl acetate (EVA), polyurethane (PU), poly isoprene (natural rubber), and any two or more polymer mixture that can form a flexible and tough bag (so that the plastic bag can be easily rolled or folded and sustain the weight of the substance firmly), and which is considerably suitable to sterilization (so that the special rolling plastic bag 2010 can be made sterile when constructed). Referring still to the FIG. 20, the special rolling plastic bag 2010 shows the bag in a half expanded state. The middle of the special rolling plastic bag 2010 is a special rolling site 2020. The rolling method of the special rolling plastic bag 2010 will describe in detail in FIG. 21. The mini-storage space 2050 may be used to hide the special rolling plastic bag 2010 in the center of the portably functional receptacle 2040. And a substance 2030 including homogeneous and heterogeneous substance may be collected in the special rolling plastic bag 2010. The portably functional receptacle 2040 provides a portable space that can store different kinds of functional tubes that can be used for collecting the substance 2030.

FIG. 21 illustrates a method of rolling and expanded the special rolling plastic bag 2010 in FIG. 20. As illustrated in FIG. 21, the special rolling plastic bag 2010 is rolled up from the middle site of the bag using the swirl-type rolling method toward the opened site of the bag or the sealed site of the bag. Further description of the rolling method, one side wall of the plastic bag 2010 may be rolled up along with the clockwise direction and another side wall of the plastic bag 2010 may be rolled up along with the counterclockwise direction simultaneously until the special rolling plastic bag 2010 is completely rolled up. However, the method to expand the special rolling plastic bag 2010 is by pulling gently at the same time along with a first expanded direction 2120a and a second expanded direction 2120b, showed in FIG. 21. For example, the first expanded direction 2120a may be operated from a rolling center 2120 towards the opened site of the special rolling plastic bag 2010 and the second expanded direction 2120b may be operated from the rolling center 2020 toward the sealed site of the special rolling plastic bag 2010. These two pulling force of opposite and parallel directions is operated to expand the special rolling plastic bag 2010 quickly.

FIG. 22 is the perspective view of expanding the special rolling plastic bag 2010, combined with the portably functional receptacle 2040 for collecting the substance 2030. As show in FIG. 22, the opened site of the special rolling plastic bag 2010 is fixed and integrated with the portably functional receptacle 2040. In the embodiment illustrated in FIG. 22, when the user wants to collect the substance 2030, the user brings two fingertips to gently pull a sealed site 3100 of the special rolling plastic bag 2010 from mini-storage space 2050 of the portably functional receptacle 2040, and expands both rolling sides of the plastic bag 2100 and 2110 to recover the original shape of the special rolling plastic bag 2010. After expanding the bag, the user may take a tube out of the portably functional receptacle 2040 to implement the drainage and collection of the substance 130 into the special rolling plastic bag 2010 conveniently.

While the present disclosure has been described with reference to various embodiments, these embodiments are illustrative, and the scope of the disclosure is not limited to them. Many variations, modifications, additions, and improvements are possible. More generally, embodiments in accordance with the present disclosure have been described in the context of particular embodiments. Functionality may be separated or combined in procedures differently in various embodiments of the disclosure or described with different terminology. These and other variations, modifications, additions, and improvements may fall within the scope of the disclosure as defined in the claims that follow.

We claim:

1. A urinary catheter and enclosure system, the system comprising:
   a urinary catheter having a distal end configured for insertion into a urethra and a proximal end;
   a sheath slidably disposed over the urinary catheter at or near the distal end of the urinary catheter, wherein the sheath is configured to slide proximally along the urinary catheter during insertion of the urinary catheter into the urethra, so that the urinary catheter can be inserted without touching the catheter;
   a donut-shaped enclosure for enclosing the urinary catheter, the enclosure comprising:
      a bottom member, comprising:
         a bottom surface; and
         an inner peripheral wall extending upward from the bottom surface to form an open inner space outside of, and in the center of, the enclosure, the inner peripheral wall defining an inner hole leading to the open inner space, wherein the proximal end of the urinary catheter extends through the inner hole and into the open inner space, so that the proximal end is located outside of the enclosure;
      a top member rotatably coupled with the bottom member such that it rotates relative to the bottom member about an axis of rotation drawn through the center of the enclosure, wherein the top member comprises:
         a top surface;
         an outer peripheral wall extending downward from the top surface to the bottom surface of the bottom member, the outer peripheral wall defining an outer hole configured to allow advancement of the urinary catheter distal end therethrough; and
         a flexible, pinching handle in the outer peripheral wall, the handle comprising a free edge ending at the outer hole, wherein the free edge of the handle is configured to move radially inward when force is applied to it, to pinch the urinary catheter and thus prevent the urinary catheter from moving back into the enclosure
      wherein rotating the top member relative to the bottom member causes the urinary catheter to wind into a spiral within the enclosure; and
   a plug formed as an integral, protruding, dome-shaped feature on the inner peripheral wall of the enclosure, across from the inner hole, wherein the plug is inserted into and seals the proximal end of the urinary catheter until the proximal end is disengaged from the plug to allow urine to flow through the proximal end.

2. The system of claim 1, further comprising a funnel attached to the proximal end of the urinary catheter, wherein the plug fits into and seals a proximal end of the funnel.

3. The system of claim 1, wherein the handle has a default open position, and wherein, when the handle is released, the outer hole is fully open to allow the urinary catheter to be moved through the outer hole.

4. The system of claim 1, wherein the outer hole is defined as opening between the free edge of the handle and an opposite end of the outer peripheral wall.

5. The system of claim 1, wherein the handle is formed partially by a cutout portion in the top surface of the top member.

6. The system of claim 1, wherein the handle comprises a gripping feature for facilitating application of the force by a finger of a user.

* * * * *